United States Patent [19]
Concannon

[11] Patent Number: 5,770,372
[45] Date of Patent: Jun. 23, 1998

[54] DETECTION OF MUTATIONS IN THE HUMAN ATM GENE

[75] Inventor: Patrick Concannon, Bainbridge Island, Wash.

[73] Assignee: Virginia Mason Research Center, Seattle, Wash.

[21] Appl. No.: 753,147

[22] Filed: Nov. 20, 1996

[51] Int. Cl.[6] .............................. C12Q 1/68; C07H 21/02; C07H 21/04
[52] U.S. Cl. .............................. 435/6; 536/23.1; 536/24.3
[58] Field of Search .............................. 435/6; 536/23.1, 536/24.3

[56] References Cited

FOREIGN PATENT DOCUMENTS

WO96/36691 A1 11/1996 WIPO.
WO96/36695 A1 11/1996 WIPO.

OTHER PUBLICATIONS

Savinsky et al., Science 268: 1749–1753 (Jun. 1993).
Wright et al., American J. Human Genetics 59(4): 839–846 (1996).
Byrd, P.J., et al., "Mutations revealed by sequencing the 5' half of the gene for ataxia telangiectasia," *Human Molecular Genetics* 5:145–149 (1996).
Gatti, R.A., et al., "Localization of an ataxia–telangiectasia gene to chromosome 11q22–23," *Nature* 336:577–580 (1988).
Gilad, S., et al., "Predominance of null mutations in ataxia–telangiectasia," *Human Molecular Genetics* 5:433–439 (1996).
Lange, E., et al., "Localization of an ataxia–telangiectasia gene to an ~500–kb interval on chromosome 11q23.1: Linkage analysis of 176 families by an international consortium," *Am. J. Hum. Genet.* 57:112–119 (1995).

Norman, A., et al., "Cancer management controversy: The importance of genetics for the optimization of radiation therapy," *Am. J. Clin. Oncol.* (CCT) 11(1):84–88 (1988).
Nowak, R., "Discovery of AT gene sparks biomedical research bonanza," *Science* 268:1700–1701 (1995).
Pippard, E.C., et al., "Cancer in homozygotes and heterozygotes of ataxia–telangiectasia and xeroderma pigmentation in Britain," *Cancer Research* 48:2929–2932 (1988).
Rasio, D., et al., "Genomic organization of the ATM locus involved in ataxia–telangiectasia," *Cancer Research* 55:6053–6057 (1995).
Savitsky, K., et al., "A single ataxia telangiectasia gene with a product similar to PI–3 kinase," *Science* 268:1749–1753 (1995a).
Savitsky, K., et al., "The complete sequence of the coding region of the ATM gene reveals similarity to cell cycle regulators in different species," *Human Molecular Genetics* 4:2025–2032 (1995b).
Swift, M., et al., "Incidence of cancer of 161 families affected by ataxia–telangiectasia," *N. Eng. J. Med.* 325:1831–1836 (1991).
Swift, M., et al., "Breast and other cancers in families with ataxia–telangiectasia," *N. Eng. J. Med.* 316:1289–1294 (1987).

(List continued on next page.)

*Primary Examiner*—Stephanie W. Zitomer
*Assistant Examiner*—Ethan Whisenant
*Attorney, Agent, or Firm*—Christensen O'Connor Johnson & Kindness PLLC

[57] ABSTRACT

This invention pertains to methods for detecting mutations in the human ataxia telangiectasia (ATM) gene. The invention provides DNA sequences immediately flanking the exons in the 3' half of the gene. Also provided are primers that can be used in the polymerase chain reaction to amplify segments of the ATM gene corresponding to each of the 65 coding exons including its immediately flanking sequences. A number of mutations found in the human ATM gene are described also.

6 Claims, 1 Drawing Sheet

OTHER PUBLICATIONS

Telatar, M., et al., "Ataxia–telangiectasia: Mutations in ATM cDNA detected by protein–truncation screening," *Am. J. Hum. Genet.* 59:40–44 (1996).

Uziel, T., et al., "Genomic organization of the ATM gene," *Genomics* 33:317–320 (1996).

Vanagaite, L., et al., "A high–density microsatellite map of the ataxia–telangiectasia locus," *Hum. Genet.* 95:451–454 (1995).

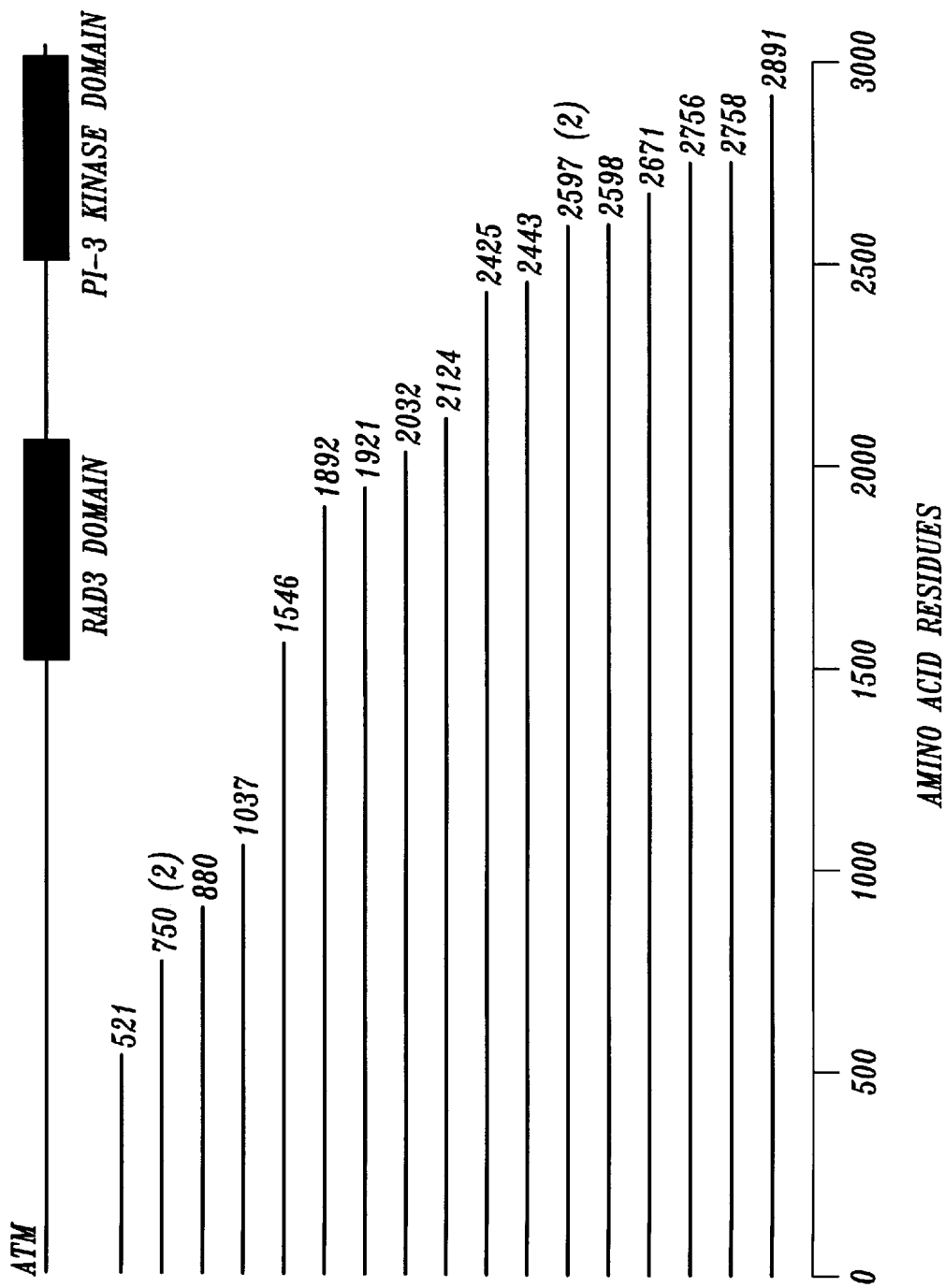

SEQUENCE LISTING ( 1 ) GENERAL INFORMATION:

( i i i ) NUMBER OF SEQUENCES: 196

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:1:

C C T C T T T C T C    T C T A T A T A T G    C             2 1

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Homo sapiens ( x i ) SEQUENCE DESCRIPTION: SEQ ID NO:2:

AATAATGGGT TACTAATCAC A  21

( 2 ) INFORMATION FOR SEQ ID NO:3:

( i ) SEQUENCE CHARACTERISTICS:
                ( A ) LENGTH: 22 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Homo sapiens ( x i ) SEQUENCE DESCRIPTION: SEQ ID NO:3:

CAATTTTTCC TTGAAATGTG TG  22

( 2 ) INFORMATION FOR SEQ ID NO:4:

( i ) SEQUENCE CHARACTERISTICS:
                ( A ) LENGTH: 23 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Homo sapiens ( x i ) SEQUENCE DESCRIPTION: SEQ ID NO:4:

CAACAGAAAT AAATATGAAA GAG  23

( 2 ) INFORMATION FOR SEQ ID NO:5:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Homo sapiens ( x i ) SEQUENCE DESCRIPTION: SEQ ID NO:5:

GATGGCATGA ACAGCTTTTG  20

( 2 ) INFORMATION FOR SEQ ID NO:6:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:6:

CTCACGCGAC AGTAATCTG         19

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:7:

TAGTTGCCAT TCCAAGTGTC         20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:8:

TGAAGTTTCA TTTCATGAGG         20

( 2 ) INFORMATION FOR SEQ ID NO:9:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO (iv) ANTI-SENSE: NO (vi) ORIGINAL SOURCE:
                (A) ORGANISM: Homo sapiens (xi) SEQUENCE DESCRIPTION: SEQ ID NO:9:

TTTTCTGTA TGGGATTATG GA                                                                         22

(2) INFORMATION FOR SEQ ID NO:10:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (vi) ORIGINAL SOURCE:
                (A) ORGANISM: Homo sapiens (xi) SEQUENCE DESCRIPTION: SEQ ID NO:10:

CATGGTCTTG CAAGATC                                                                               17

(2) INFORMATION FOR SEQ ID NO:11:

(i) SEQUENCE CHARACTERISTICS:
                (A) LENGTH: 19 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (vi) ORIGINAL SOURCE:
                (A) ORGANISM: Homo sapiens (xi) SEQUENCE DESCRIPTION: SEQ ID NO:11:

CCCCCTGTTA TACCCAGTT                                                                             19

(2) INFORMATION FOR SEQ ID NO:12:

(i) SEQUENCE CHARACTERISTICS:
                (A) LENGTH: 22 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (vi) ORIGINAL SOURCE:
                (A) ORGANISM: Homo sapiens (xi) SEQUENCE DESCRIPTION: SEQ ID NO:12:

TGAAGAAGCA AATTCAAAAC AG                                                                         22

(2) INFORMATION FOR SEQ ID NO:13:

(i) SEQUENCE CHARACTERISTICS:
                (A) LENGTH: 20 base pairs (B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO:13:

TTTGTGGGGA GCTAGCAGTG 20

(2) INFORMATION FOR SEQ ID NO:14:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO:14:

AAAAGCCCAA ATGCCCAG 18

(2) INFORMATION FOR SEQ ID NO:15:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO:15:

AACAGCGAAA CTCTGGCTC 19

(2) INFORMATION FOR SEQ ID NO:16:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO:16:

ACAAGAGATT AAAATGACAC T    21

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:17:

GTTTGTTAAT GTGATGGAAT A    21

( 2 ) INFORMATION FOR SEQ ID NO:18:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:18:

GTGTGTTTAT CTGTAAGTCA G    21

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:19:

ATAAAGTCTT TGCCCCTCCA    20

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:20:

AAATAAGTGG AGAGAGCCTG  20

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:21:

GGCTTTTGGT CTTCTAAGTG  20

( 2 ) INFORMATION FOR SEQ ID NO:22:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:22:

ATCTTTGTAA TTAAAGCTAT AGC  23

( 2 ) INFORMATION FOR SEQ ID NO:23:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:23:

GTAGTCTTTG AATGATGTAG A  21

( 2 ) INFORMATION FOR SEQ ID NO:24:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Homo sapiens ( x i ) SEQUENCE DESCRIPTION: SEQ ID NO:24:

CTATTTCTCC TTCCTAACAG T  21

( 2 ) INFORMATION FOR SEQ ID NO:25:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Homo sapiens ( x i ) SEQUENCE DESCRIPTION: SEQ ID NO:25:

TTCTTACAAA AGATAGAGTA T  21

( 2 ) INFORMATION FOR SEQ ID NO:26:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Homo sapiens ( x i ) SEQUENCE DESCRIPTION: SEQ ID NO:26:

TTCCAAACAA ATGTAATAAT T  21

( 2 ) INFORMATION FOR SEQ ID NO:27:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Homo sapiens ( x i ) SEQUENCE DESCRIPTION: SEQ ID NO:27:

CCAAGATCAA AGTACACTGT A                                    21

( 2 ) INFORMATION FOR SEQ ID NO:28:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:28:

CCCACTGCAC TCCAGCCTGG G                                    21

( 2 ) INFORMATION FOR SEQ ID NO:29:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:29:

ATATTGGCCC TAATAGTAAA C                                    21

( 2 ) INFORMATION FOR SEQ ID NO:30:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:30:

CTTATTTACA AAGATATTTC A                                    21

( 2 ) INFORMATION FOR SEQ ID NO:31:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:31:

AATTGCTGAG ATTACAGATG T 21

( 2 ) INFORMATION FOR SEQ ID NO:32:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:32:

ACTAAACCGT CATATTCTCC G 21

( 2 ) INFORMATION FOR SEQ ID NO:33:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:33:

ATATAATTAA TTTCACTATA A 21

( 2 ) INFORMATION FOR SEQ ID NO:34:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:34:

TACATTTAGT CAGCAACATC A 21

( 2 ) INFORMATION FOR SEQ ID NO:35:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:35:

CCGGCCTATG TTTATATACT T        21

( 2 ) INFORMATION FOR SEQ ID NO:36:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:36:

TTAACAGAAC ACATCAGTTA T        21

( 2 ) INFORMATION FOR SEQ ID NO:37:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:37:

AAAGTTATAA AATAACTGAT G        21

( 2 ) INFORMATION FOR SEQ ID NO:38:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO (vi) ORIGINAL SOURCE:
            (A) ORGANISM: Homo sapiens (xi) SEQUENCE DESCRIPTION: SEQ ID NO:38:

CTTGCATTCG TATCCACAGA T                    21

(2) INFORMATION FOR SEQ ID NO:39:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:39:

TTAGCACAGA AAGACATATT G                    21

(2) INFORMATION FOR SEQ ID NO:40:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:40:

AATTACTCAT TAACAAACAA A                    21

(2) INFORMATION FOR SEQ ID NO:41:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:41:

GCAGTCTTTG TTTGTTAATG A                    21

(2) INFORMATION FOR SEQ ID NO:42:

(i) SEQUENCE CHARACTERISTICS:
            (A) LENGTH: 21 base pairs
            (B) TYPE: nucleic acid
            (C) STRANDEDNESS: single ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                    ( A ) ORGANISM: Homo sapiens ( x i ) SEQUENCE DESCRIPTION: SEQ ID NO:42:

CTATGTAAGA CATTCTACTG C                                                            2 1

( 2 ) INFORMATION FOR SEQ ID NO:43:

( i ) SEQUENCE CHARACTERISTICS:
                    ( A ) LENGTH: 20 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                    ( A ) ORGANISM: Homo sapiens ( x i ) SEQUENCE DESCRIPTION: SEQ ID NO:43:

GTTTGTTTGC TTGCTTGTTT                                                              2 0

( 2 ) INFORMATION FOR SEQ ID NO:44:

( i ) SEQUENCE CHARACTERISTICS:
                    ( A ) LENGTH: 20 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                    ( A ) ORGANISM: Homo sapiens ( x i ) SEQUENCE DESCRIPTION: SEQ ID NO:44:

ATTTATGGGA TATTCATAGC                                                              2 0

( 2 ) INFORMATION FOR SEQ ID NO:45:

( i ) SEQUENCE CHARACTERISTICS:
                    ( A ) LENGTH: 21 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                    ( A ) ORGANISM: Homo sapiens ( x i ) SEQUENCE DESCRIPTION: SEQ ID NO:45:

TGGAGTTCAG TTGGGATTTT A                                                            2 1

( 2 ) INFORMATION FOR SEQ ID NO:46:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:46:

TTCACAGTGA CCTAAGGAAG C    21

( 2 ) INFORMATION FOR SEQ ID NO:47:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:47:

GTTGTTTCTA GGTCCTACTC T    21

( 2 ) INFORMATION FOR SEQ ID NO:48:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:48:

GACTTGCTAA GTATTGTTAA C    21

( 2 ) INFORMATION FOR SEQ ID NO:49:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:49:

TGATACTTTA ATGCTGATGG T 21

( 2 ) INFORMATION FOR SEQ ID NO:50:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:50:

GGTTATATCT CATATCATTC A 21

( 2 ) INFORMATION FOR SEQ ID NO:51:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:51:

TCCTCTTAGT CTACAGGTTG 20

( 2 ) INFORMATION FOR SEQ ID NO:52:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:52:

GACATTGAAG GTGTCAACCA 20

( 2 ) INFORMATION FOR SEQ ID NO:53:

( i ) SEQUENCE CHARACTERISTICS:
        ( A ) LENGTH: 20 base pairs (B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Homo sapiens (xi) SEQUENCE DESCRIPTION: SEQ ID NO:53:

TGGAAGTTCA CTGGTCTATG      20

(2) INFORMATION FOR SEQ ID NO:54:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Homo sapiens (xi) SEQUENCE DESCRIPTION: SEQ ID NO:54:

TACTTTTCCT CTTTAAGATG TAT      23

(2) INFORMATION FOR SEQ ID NO:55:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Homo sapiens (xi) SEQUENCE DESCRIPTION: SEQ ID NO:55:

TTTATTGTAG CCGAGTATCT AA      22

(2) INFORMATION FOR SEQ ID NO:56:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Homo sapiens (xi) SEQUENCE DESCRIPTION: SEQ ID NO:56:

AAACAGGAAG AACAGGATAG A    21

(2) INFORMATION FOR SEQ ID NO:57:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:57:

TGCTGAACCA AAGGACTTCT    20

(2) INFORMATION FOR SEQ ID NO:58:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:58:

CACTCAAATC CTTCTAACAA TA    22

(2) INFORMATION FOR SEQ ID NO:59:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:59:

CAGTAAGTTT TGTTGGCTTA C    21

(2) INFORMATION FOR SEQ ID NO:60:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:60:

CTGCTAGAGC ATTACAGATT T 21

( 2 ) INFORMATION FOR SEQ ID NO:61:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:61:

TGTCTATAAA TGGCACTTAA CT 22

( 2 ) INFORMATION FOR SEQ ID NO:62:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:62:

CCAAGAGCAA GACTTTGCC 19

( 2 ) INFORMATION FOR SEQ ID NO:63:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:63:

TAGAAGTTTT CTAGTCAGAT AAT 23

( 2 ) INFORMATION FOR SEQ ID NO:64:

(  i  ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear (  i i  ) MOLECULE TYPE: DNA (genomic)

(  i i i  ) HYPOTHETICAL: NO (  i v  ) ANTI-SENSE: NO (  v i  ) ORIGINAL SOURCE:
        ( A ) ORGANISM: Homo sapiens (  x i  ) SEQUENCE DESCRIPTION: SEQ ID NO:64:

AATCTGTCCT ATATGTGATC C                    21

( 2 ) INFORMATION FOR SEQ ID NO:65:

(  i  ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear (  i i  ) MOLECULE TYPE: DNA (genomic)

(  i i i  ) HYPOTHETICAL: NO (  i v  ) ANTI-SENSE: NO (  v i  ) ORIGINAL SOURCE:
        ( A ) ORGANISM: Homo sapiens (  x i  ) SEQUENCE DESCRIPTION: SEQ ID NO:65:

CTTGAAGTAC AGAAAAACAG C                    21

( 2 ) INFORMATION FOR SEQ ID NO:66:

(  i  ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear (  i i  ) MOLECULE TYPE: DNA (genomic)

(  i i i  ) HYPOTHETICAL: NO (  i v  ) ANTI-SENSE: NO (  v i  ) ORIGINAL SOURCE:
        ( A ) ORGANISM: Homo sapiens (  x i  ) SEQUENCE DESCRIPTION: SEQ ID NO:66:

GTATCATTCT CCATGAATGT C                    21

( 2 ) INFORMATION FOR SEQ ID NO:67:

(  i  ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear (  i i  ) MOLECULE TYPE: DNA (genomic)

(  i i i  ) HYPOTHETICAL: NO (  i v  ) ANTI-SENSE: NO (  v i  ) ORIGINAL SOURCE:
        ( A ) ORGANISM: Homo sapiens ( x i ) SEQUENCE DESCRIPTION: SEQ ID NO:67:

TGGAGGTTAA CATTCATCAA G 21

( 2 ) INFORMATION FOR SEQ ID NO:68:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:68:

ATTTAACAGT CATGACCCAC A 21

( 2 ) INFORMATION FOR SEQ ID NO:69:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:69:

GGAAAGGTAC AATGATTTCC A 21

( 2 ) INFORMATION FOR SEQ ID NO:70:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:70:

ATGTGCAGTA TCACAGCACT 20

( 2 ) INFORMATION FOR SEQ ID NO:71:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:71:

GTATGTTGAG TTTATGGCAG A    21

( 2 ) INFORMATION FOR SEQ ID NO:72:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:72:

ATCCATCTTT CTCTAGAACT G    21

( 2 ) INFORMATION FOR SEQ ID NO:73:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:73:

ACCAGAACCT TATAGCATAG T    21

( 2 ) INFORMATION FOR SEQ ID NO:74:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:74:

TTCAGCCGAT AGTTAACAAG T    21

( 2 ) INFORMATION FOR SEQ ID NO:75:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:75:

TAAGCAGTCA CTACCATTGT A        21

( 2 ) INFORMATION FOR SEQ ID NO:76:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:76:

ATACCCTTAT TGAGACAATG C        21

( 2 ) INFORMATION FOR SEQ ID NO:77:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:77:

GTATATGTAT TCAGGAGCTT C        21

( 2 ) INFORMATION FOR SEQ ID NO:78:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Homo sapiens ( x i ) SEQUENCE DESCRIPTION: SEQ ID NO:78:

ATGGCATCTG TACAGTGTCT 20

( 2 ) INFORMATION FOR SEQ ID NO:79:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:79:

CAGAACTGTA TTTCAGAATC AT 22

( 2 ) INFORMATION FOR SEQ ID NO:80:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:80:

ACATAACTCC TTCATAAACA GA 22

( 2 ) INFORMATION FOR SEQ ID NO:81:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:81:

CCAAAGCTAT TTTCACAATC TT 22

( 2 ) INFORMATION FOR SEQ ID NO:82:

( i ) SEQUENCE CHARACTERISTICS:
    ( A ) LENGTH: 21 base pairs
    ( B ) TYPE: nucleic acid
    ( C ) STRANDEDNESS: single (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:82:

TACTGAAATA ACCTCAGCAC T                                                                 21

(2) INFORMATION FOR SEQ ID NO:83:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:83:

CTCTGGTTTT CTGTTGATAT C                                                                 21

(2) INFORMATION FOR SEQ ID NO:84:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:84:

CCCCATGAAG AATCAAGTC                                                                    19

(2) INFORMATION FOR SEQ ID NO:85:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:85:

TTTATACATG TATATCTTAG GGTTCTG                                                           27

( 2 ) INFORMATION FOR SEQ ID NO:86:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:86:

TTCAGAAAAG AAGCCATGAC A      21

( 2 ) INFORMATION FOR SEQ ID NO:87:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:87:

TATTTCCCTG AAAACCTCTT C      21

( 2 ) INFORMATION FOR SEQ ID NO:88:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:88:

CACTATTGGT AACAGAAAAG C      21

( 2 ) INFORMATION FOR SEQ ID NO:89:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                        ( A ) ORGANISM: Homo sapiens ( x i ) SEQUENCE DESCRIPTION: SEQ ID NO:89:

TCATTTCTCT TGCTTACATG AA                                                                                22

( 2 ) INFORMATION FOR SEQ ID NO:90:

( i ) SEQUENCE CHARACTERISTICS:
                        ( A ) LENGTH: 21 base pairs
                        ( B ) TYPE: nucleic acid
                        ( C ) STRANDEDNESS: single
                        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                        ( A ) ORGANISM: Homo sapiens ( x i ) SEQUENCE DESCRIPTION: SEQ ID NO:90:

AAAGGAAAGT CAAGAGGTAA G                                                                                 21

( 2 ) INFORMATION FOR SEQ ID NO:91:

( i ) SEQUENCE CHARACTERISTICS:
                        ( A ) LENGTH: 21 base pairs
                        ( B ) TYPE: nucleic acid
                        ( C ) STRANDEDNESS: single
                        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                        ( A ) ORGANISM: Homo sapiens ( x i ) SEQUENCE DESCRIPTION: SEQ ID NO:91:

ATGGTAGTTG CTGCTTTCAT T                                                                                 21

( 2 ) INFORMATION FOR SEQ ID NO:92:

( i ) SEQUENCE CHARACTERISTICS:
                        ( A ) LENGTH: 23 base pairs
                        ( B ) TYPE: nucleic acid
                        ( C ) STRANDEDNESS: single
                        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                        ( A ) ORGANISM: Homo sapiens ( x i ) SEQUENCE DESCRIPTION: SEQ ID NO:92:

TTACTAATTT CAAGGCTCTA ATA                                                                               23

( 2 ) INFORMATION FOR SEQ ID NO:93:

( i ) SEQUENCE CHARACTERISTICS:
                        ( A ) LENGTH: 20 base pairs ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:93:

AGTTGGGTAC AGTCATGGTA 20

( 2 ) INFORMATION FOR SEQ ID NO:94:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:94:

GAAAAGATGA AGCATATTCA TG 22

( 2 ) INFORMATION FOR SEQ ID NO:95:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:95:

TTTGAGTGAT TCTTTAGATG TAT 23

( 2 ) INFORMATION FOR SEQ ID NO:96:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:96:

AACAACTCAC TCAGTTAACT G    21

( 2 ) INFORMATION FOR SEQ ID NO:97:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:97:

TGTGTGATTT TGTAGTTCTG TT    22

( 2 ) INFORMATION FOR SEQ ID NO:98:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:98:

ACATCAAGGG GCTTATGTCT    20

( 2 ) INFORMATION FOR SEQ ID NO:99:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:99:

ACTTACTTGC TTAGATGTGA G    21

( 2 ) INFORMATION FOR SEQ ID NO:100:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

(iii) HYPOTHETICAL: NO (iv) ANTI-SENSE: NO (vi) ORIGINAL SOURCE:
 (A) ORGANISM: Homo sapiens (xi) SEQUENCE DESCRIPTION: SEQ ID NO:100:

CCATTTCTTA GAGGGAATGG 20

(2) INFORMATION FOR SEQ ID NO:101:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (vi) ORIGINAL SOURCE:
  (A) ORGANISM: Homo sapiens (xi) SEQUENCE DESCRIPTION: SEQ ID NO:101:

CACTGCAGTA TCTAGACAGT 20

(2) INFORMATION FOR SEQ ID NO:102:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (vi) ORIGINAL SOURCE:
  (A) ORGANISM: Homo sapiens (xi) SEQUENCE DESCRIPTION: SEQ ID NO:102:

CTAGGAAAGA CTGAATATCA C 21

(2) INFORMATION FOR SEQ ID NO:103:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (vi) ORIGINAL SOURCE:
  (A) ORGANISM: Homo sapiens (xi) SEQUENCE DESCRIPTION: SEQ ID NO:103:

AATGTTGGGT AGTTCCTTAT G 21

(2) INFORMATION FOR SEQ ID NO:104:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:104:

GCTTTTGGAT TACGTTTGTG A 21

( 2 ) INFORMATION FOR SEQ ID NO:105:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:105:

TGACTATTCC TGCTTGACCT 20

( 2 ) INFORMATION FOR SEQ ID NO:106:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:106:

TTTCACCAAT TTTGACCTAC AT 22

( 2 ) INFORMATION FOR SEQ ID NO:107:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:107:

TAACCACTAT CACATCGTCA T                    21

( 2 ) INFORMATION FOR SEQ ID NO:108:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:108:

CTTCCTCATT TGTAAGTATT CA                   22

( 2 ) INFORMATION FOR SEQ ID NO:109:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:109:

CCTTTGCTAT TCTCAGATGA CTCTGT               26

( 2 ) INFORMATION FOR SEQ ID NO:110:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:110:

GCATTATGAA TATGGGCATG A                    21

( 2 ) INFORMATION FOR SEQ ID NO:111:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:111:

GATCATCAAA TGCTCTTTAA TG                22

( 2 ) INFORMATION FOR SEQ ID NO:112:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:112:

TATCTGACAG CTGTCAGCTT                20

( 2 ) INFORMATION FOR SEQ ID NO:113:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:113:

GTGTATATTA GTTTAATTGA ACAC              24

( 2 ) INFORMATION FOR SEQ ID NO:114:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:114:

AACCTGCCAA ACAACAAAGT G                21

( 2 ) INFORMATION FOR SEQ ID NO:115:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:115:

TAGAAAGAGA TGGAATCAGT G                        21

( 2 ) INFORMATION FOR SEQ ID NO:116:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:116:

ATCTTGGTAG GCAAACAACA T                        21

( 2 ) INFORMATION FOR SEQ ID NO:117:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:117:

AAAGTTCACA TTCTAACTGG AA                       22

( 2 ) INFORMATION FOR SEQ ID NO:118:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:118:

ATTACAGGTG CAAAGAACCA T               21

( 2 ) INFORMATION FOR SEQ ID NO:119:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:119:

GATAAAGATA CGTTGACAAC ATTGG            25

( 2 ) INFORMATION FOR SEQ ID NO:120:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:120:

GTGACTTCCT GATGAGATAC ACAG             24

( 2 ) INFORMATION FOR SEQ ID NO:121:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:121:

CTGGTTCTAC TGTTTCTAAG T                21

( 2 ) INFORMATION FOR SEQ ID NO:122:

( i ) SEQUENCE CHARACTERISTICS:
        ( A ) LENGTH: 20 base pairs
        ( B ) TYPE: nucleic acid
        ( C ) STRANDEDNESS: single ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
            ( A ) ORGANISM: Homo sapiens ( x i ) SEQUENCE DESCRIPTION: SEQ ID NO:122:

GTTTCAGTGA GGTGAACAGT 20

( 2 ) INFORMATION FOR SEQ ID NO:123:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
            ( A ) ORGANISM: Homo sapiens ( x i ) SEQUENCE DESCRIPTION: SEQ ID NO:123:

TCCTGTTGTC AGTTTTTCAG A 21

( 2 ) INFORMATION FOR SEQ ID NO:124:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
            ( A ) ORGANISM: Homo sapiens ( x i ) SEQUENCE DESCRIPTION: SEQ ID NO:124:

ACTTAAAGTA TGTTGGCAGG T 21

( 2 ) INFORMATION FOR SEQ ID NO:125:

( i ) SEQUENCE CHARACTERISTICS:
            ( A ) LENGTH: 16 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
            ( A ) ORGANISM: Homo sapiens ( x i ) SEQUENCE DESCRIPTION: SEQ ID NO:125:

TTCAGGGTAT GTACAT 16

( 2 ) INFORMATION FOR SEQ ID NO:126:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:126:

ACTCTGTTAG GGATTT     16

( 2 ) INFORMATION FOR SEQ ID NO:127:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:127:

AGCCCTGTAA GTATAC     16

( 2 ) INFORMATION FOR SEQ ID NO:128:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:128:

TATTTCTAG GATTCC     16

( 2 ) INFORMATION FOR SEQ ID NO:129:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Homo sapiens ( x i ) SEQUENCE DESCRIPTION: SEQ ID NO:129:

AGCCCTGTAA ATAACA                                                               16

( 2 ) INFORMATION FOR SEQ ID NO:130:

( i ) SEQUENCE CHARACTERISTICS:
                ( A ) LENGTH: 16 base pairs
                ( B ) TYPE: nucleic acid
                ( C ) STRANDEDNESS: double
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Homo sapiens ( x i ) SEQUENCE DESCRIPTION: SEQ ID NO:130:

CCTATATTAG GCCTTC                                                               16

( 2 ) INFORMATION FOR SEQ ID NO:131:

( i ) SEQUENCE CHARACTERISTICS:
                ( A ) LENGTH: 16 base pairs
                ( B ) TYPE: nucleic acid
                ( C ) STRANDEDNESS: double
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Homo sapiens ( x i ) SEQUENCE DESCRIPTION: SEQ ID NO:131:

AAACAGGTAA TTTTCT                                                               16

( 2 ) INFORMATION FOR SEQ ID NO:132:

( i ) SEQUENCE CHARACTERISTICS:
                ( A ) LENGTH: 16 base pairs
                ( B ) TYPE: nucleic acid
                ( C ) STRANDEDNESS: double
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Homo sapiens ( x i ) SEQUENCE DESCRIPTION: SEQ ID NO:132:

TTATATTTAG GTATTG                                                               16

( 2 ) INFORMATION FOR SEQ ID NO:133:

( i ) SEQUENCE CHARACTERISTICS:
                ( A ) LENGTH: 16 base pairs ( B ) TYPE: nucleic acid
                    ( C ) STRANDEDNESS: double
                    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                    ( A ) ORGANISM: Homo sapiens ( x i ) SEQUENCE DESCRIPTION: SEQ ID NO:133:

TTGGAGGTAA TAAAAA                                                                                16

( 2 ) INFORMATION FOR SEQ ID NO:134:

( i ) SEQUENCE CHARACTERISTICS:
                    ( A ) LENGTH: 16 base pairs
                    ( B ) TYPE: nucleic acid
                    ( C ) STRANDEDNESS: double
                    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                    ( A ) ORGANISM: Homo sapiens ( x i ) SEQUENCE DESCRIPTION: SEQ ID NO:134:

TCTCTTTTAG GAAATT                                                                                16

( 2 ) INFORMATION FOR SEQ ID NO:135:

( i ) SEQUENCE CHARACTERISTICS:
                    ( A ) LENGTH: 16 base pairs
                    ( B ) TYPE: nucleic acid
                    ( C ) STRANDEDNESS: double
                    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                    ( A ) ORGANISM: Homo sapiens ( x i ) SEQUENCE DESCRIPTION: SEQ ID NO:135:

CTCAGGGTGC TAATTT                                                                                16

( 2 ) INFORMATION FOR SEQ ID NO:136:

( i ) SEQUENCE CHARACTERISTICS:
                    ( A ) LENGTH: 16 base pairs
                    ( B ) TYPE: nucleic acid
                    ( C ) STRANDEDNESS: double
                    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                    ( A ) ORGANISM: Homo sapiens ( x i ) SEQUENCE DESCRIPTION: SEQ ID NO:136:

ATATTTCTAG ATAATC                                                          16

( 2 ) INFORMATION FOR SEQ ID NO:137:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:137:

TTCTAGGTAA ACTACA                                                          16

( 2 ) INFORMATION FOR SEQ ID NO:138:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:138:

CTATATGTAG AGGCTG                                                          16

( 2 ) INFORMATION FOR SEQ ID NO:139:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:139:

AGATTGGTGA GTATTT                                                          16

( 2 ) INFORMATION FOR SEQ ID NO:140:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:140:

TTTTTTTCAG TGTCAA 16

( 2 ) INFORMATION FOR SEQ ID NO:141:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:141:

AAAAGGTCT CTTAAG 16

( 2 ) INFORMATION FOR SEQ ID NO:142:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:142:

TTCTTTCTAG TTTTTA 16

( 2 ) INFORMATION FOR SEQ ID NO:143:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:143:

TGTGAAGTAA GAAGAT 16

( 2 ) INFORMATION FOR SEQ ID NO:144:

( i ) SEQUENCE CHARACTERISTICS:
  ( A ) LENGTH: 16 base pairs
  ( B ) TYPE: nucleic acid
  ( C ) STRANDEDNESS: double
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Homo sapiens ( x i ) SEQUENCE DESCRIPTION: SEQ ID NO:144:

TATATTCTAG GTGAAA 16

( 2 ) INFORMATION FOR SEQ ID NO:145:

( i ) SEQUENCE CHARACTERISTICS:
  ( A ) LENGTH: 16 base pairs
  ( B ) TYPE: nucleic acid
  ( C ) STRANDEDNESS: double
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Homo sapiens ( x i ) SEQUENCE DESCRIPTION: SEQ ID NO:145:

ATTCAGGTAT TCTATT 16

( 2 ) INFORMATION FOR SEQ ID NO:146:

( i ) SEQUENCE CHARACTERISTICS:
  ( A ) LENGTH: 16 base pairs
  ( B ) TYPE: nucleic acid
  ( C ) STRANDEDNESS: double
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Homo sapiens ( x i ) SEQUENCE DESCRIPTION: SEQ ID NO:146:

TGTTTGTCAG AGTCAG 16

( 2 ) INFORMATION FOR SEQ ID NO:147:

( i ) SEQUENCE CHARACTERISTICS:
  ( A ) LENGTH: 16 base pairs
  ( B ) TYPE: nucleic acid
  ( C ) STRANDEDNESS: double
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Homo sapiens ( x i ) SEQUENCE DESCRIPTION: SEQ ID NO:147:

AAAGAGGTAA TGTAAT 16

( 2 ) INFORMATION FOR SEQ ID NO:148:

( i ) SEQUENCE CHARACTERISTICS:
  ( A ) LENGTH: 16 base pairs
  ( B ) TYPE: nucleic acid
  ( C ) STRANDEDNESS: double
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Homo sapiens ( x i ) SEQUENCE DESCRIPTION: SEQ ID NO:148:

TTTTCTTTAG ACCTTC 16

( 2 ) INFORMATION FOR SEQ ID NO:149:

( i ) SEQUENCE CHARACTERISTICS:
  ( A ) LENGTH: 16 base pairs
  ( B ) TYPE: nucleic acid
  ( C ) STRANDEDNESS: double
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Homo sapiens ( x i ) SEQUENCE DESCRIPTION: SEQ ID NO:149:

GAAAAGGTAA TGGAAT 16

( 2 ) INFORMATION FOR SEQ ID NO:150:

( i ) SEQUENCE CHARACTERISTICS:
  ( A ) LENGTH: 16 base pairs
  ( B ) TYPE: nucleic acid
  ( C ) STRANDEDNESS: double
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Homo sapiens ( x i ) SEQUENCE DESCRIPTION: SEQ ID NO:150:

AGACAAACAG AAGTCT 16

( 2 ) INFORMATION FOR SEQ ID NO:151:

( i ) SEQUENCE CHARACTERISTICS:
  ( A ) LENGTH: 16 base pairs
  ( B ) TYPE: nucleic acid
  ( C ) STRANDEDNESS: double
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:151:

TTACAGGTAA ATATTA 16

( 2 ) INFORMATION FOR SEQ ID NO:152:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:152:

ATGTTTTCAG GATCTT 16

( 2 ) INFORMATION FOR SEQ ID NO:153:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:153:

TACTAGGTAA ATTGCA 16

( 2 ) INFORMATION FOR SEQ ID NO:154:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:154:

TTTCTTATAG ACTACG 16

( 2 ) INFORMATION FOR SEQ ID NO:155:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:155:

ATTCAGGTAC ATTTTT     16

( 2 ) INFORMATION FOR SEQ ID NO:156:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:156:

TCCTGTTTAG GCCTTG     16

( 2 ) INFORMATION FOR SEQ ID NO:157:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:157:

CGTCAGGTAA GAAGTG     16

( 2 ) INFORMATION FOR SEQ ID NO:158:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Homo sapiens ( x i ) SEQUENCE DESCRIPTION: SEQ ID NO:158:

TATCTCACAG CAAAGA 16

( 2 ) INFORMATION FOR SEQ ID NO:159:

( i ) SEQUENCE CHARACTERISTICS:
    ( A ) LENGTH: 16 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:159:

TGCCAGGTAT TATGAA 16

( 2 ) INFORMATION FOR SEQ ID NO:160:

( i ) SEQUENCE CHARACTERISTICS:
    ( A ) LENGTH: 16 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:160:

TTGCTACTAG AGTAAA 16

( 2 ) INFORMATION FOR SEQ ID NO:161:

( i ) SEQUENCE CHARACTERISTICS:
    ( A ) LENGTH: 16 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:161:

CTCAAGGTAT GTAATT 16

( 2 ) INFORMATION FOR SEQ ID NO:162:

( i ) SEQUENCE CHARACTERISTICS:
    ( A ) LENGTH: 16 base pairs
    ( B ) TYPE: nucleic acid
    ( C ) STRANDEDNESS: double (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Homo sapiens (xi) SEQUENCE DESCRIPTION: SEQ ID NO:162:

TGGCATTCAG ATCAGT 16

(2) INFORMATION FOR SEQ ID NO:163:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:163:

ACTCAGGTAA ATACAA 16

(2) INFORMATION FOR SEQ ID NO:164:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:164:

TTCATTTCAG CTCCCT 16

(2) INFORMATION FOR SEQ ID NO:165:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:165:

GCAGCGGTTT GTTTTT 16

( 2 ) INFORMATION FOR SEQ ID NO:166:

( i ) SEQUENCE CHARACTERISTICS:
      ( A ) LENGTH: 16 base pairs
      ( B ) TYPE: nucleic acid
      ( C ) STRANDEDNESS: double
      ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
      ( A ) ORGANISM: Homo sapiens ( x i ) SEQUENCE DESCRIPTION: SEQ ID NO:166:

TCTTATACAG AACAAT 16

( 2 ) INFORMATION FOR SEQ ID NO:167:

( i ) SEQUENCE CHARACTERISTICS:
      ( A ) LENGTH: 16 base pairs
      ( B ) TYPE: nucleic acid
      ( C ) STRANDEDNESS: double
      ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
      ( A ) ORGANISM: Homo sapiens ( x i ) SEQUENCE DESCRIPTION: SEQ ID NO:167:

GAAAAGGTAA GATTTT 16

( 2 ) INFORMATION FOR SEQ ID NO:168:

( i ) SEQUENCE CHARACTERISTICS:
      ( A ) LENGTH: 16 base pairs
      ( B ) TYPE: nucleic acid
      ( C ) STRANDEDNESS: double
      ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
      ( A ) ORGANISM: Homo sapiens ( x i ) SEQUENCE DESCRIPTION: SEQ ID NO:168:

TTTCTTGAAG GCAGTA 16

( 2 ) INFORMATION FOR SEQ ID NO:169:

( i ) SEQUENCE CHARACTERISTICS:
      ( A ) LENGTH: 16 base pairs
      ( B ) TYPE: nucleic acid
      ( C ) STRANDEDNESS: double
      ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Homo sapiens ( x i ) SEQUENCE DESCRIPTION: SEQ ID NO:169:

AAACAGGTAA CTAGGT                                                                                          16

( 2 ) INFORMATION FOR SEQ ID NO:170:

( i ) SEQUENCE CHARACTERISTICS:
                ( A ) LENGTH: 16 base pairs
                ( B ) TYPE: nucleic acid
                ( C ) STRANDEDNESS: double
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Homo sapiens ( x i ) SEQUENCE DESCRIPTION: SEQ ID NO:170:

TCTATGCAAG ATACAC                                                                                          16

( 2 ) INFORMATION FOR SEQ ID NO:171:

( i ) SEQUENCE CHARACTERISTICS:
                ( A ) LENGTH: 16 base pairs
                ( B ) TYPE: nucleic acid
                ( C ) STRANDEDNESS: double
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Homo sapiens ( x i ) SEQUENCE DESCRIPTION: SEQ ID NO:171:

ATGAAGGCAA GTGTTA                                                                                          16

( 2 ) INFORMATION FOR SEQ ID NO:172:

( i ) SEQUENCE CHARACTERISTICS:
                ( A ) LENGTH: 16 base pairs
                ( B ) TYPE: nucleic acid
                ( C ) STRANDEDNESS: double
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Homo sapiens ( x i ) SEQUENCE DESCRIPTION: SEQ ID NO:172:

TTAATGGTAG AGAGAC                                                                                          16

( 2 ) INFORMATION FOR SEQ ID NO:173:

( i ) SEQUENCE CHARACTERISTICS:
                ( A ) LENGTH: 16 base pairs (B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO:173:

AATAATGTAA GTAAAC 16

(2) INFORMATION FOR SEQ ID NO:174:

(i) SEQUENCE CHARACTERISTICS:
(A) LENGTH: 16 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO:174:

TTTCTTACAG CTAATC 16

(2) INFORMATION FOR SEQ ID NO:175:

(i) SEQUENCE CHARACTERISTICS:
(A) LENGTH: 16 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO:175:

GATGAGGTAT TTGGAT 16

(2) INFORMATION FOR SEQ ID NO:176:

(i) SEQUENCE CHARACTERISTICS:
(A) LENGTH: 16 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO:176:

TTATTAATAG GATCGA 16

( 2 ) INFORMATION FOR SEQ ID NO:177:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:177:

AGAGAAGTAT GTTTTT 16

( 2 ) INFORMATION FOR SEQ ID NO:178:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:178:

TTAAATACAG AAGGCA 16

( 2 ) INFORMATION FOR SEQ ID NO:179:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:179:

ATTAAGGTAA TTTGCA 16

( 2 ) INFORMATION FOR SEQ ID NO:180:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

(iii) HYPOTHETICAL: NO (iv) ANTI-SENSE: NO (vi) ORIGINAL SOURCE:
    (A) ORGANISM: Homo sapiens (xi) SEQUENCE DESCRIPTION: SEQ ID NO:180:

CTTTTATTAG GTGGAC      16

(2) INFORMATION FOR SEQ ID NO:181:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:181:

GTTAAGGTGA GCCTTC      16

(2) INFORMATION FOR SEQ ID NO:182:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:182:

TCTGAAGGAG GGCCGT      16

(2) INFORMATION FOR SEQ ID NO:183:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:183:

TATAAGGTAA CTATTT      16

(2) INFORMATION FOR SEQ ID NO:184:

( i ) SEQUENCE CHARACTERISTICS:
    ( A ) LENGTH: 16 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:184:

GTAACTCCAG GTGGTT  16

( 2 ) INFORMATION FOR SEQ ID NO:185:

( i ) SEQUENCE CHARACTERISTICS:
    ( A ) LENGTH: 16 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:185:

ATGATGGTGA GTGACA  16

( 2 ) INFORMATION FOR SEQ ID NO:186:

( i ) SEQUENCE CHARACTERISTICS:
    ( A ) LENGTH: 16 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:186:

CTATTTAAAG GAGGTG  16

( 2 ) INFORMATION FOR SEQ ID NO:187:

( i ) SEQUENCE CHARACTERISTICS:
    ( A ) LENGTH: 16 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:187:

CTATTGGTAA TCTTCT                                              16

( 2 ) INFORMATION FOR SEQ ID NO:188:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:188:

TTTTCTCCAG TTGGTT                                              16

( 2 ) INFORMATION FOR SEQ ID NO:189:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:189:

ATCTAGGTAA GTAAAA                                              16

( 2 ) INFORMATION FOR SEQ ID NO:190:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:190:

TTTACTTTAG GTGTTG                                              16

( 2 ) INFORMATION FOR SEQ ID NO:191:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear (  i i  ) MOLECULE TYPE: DNA (genomic)

(  i i i  ) HYPOTHETICAL: NO (  i v  ) ANTI-SENSE: NO (  v i  ) ORIGINAL SOURCE:
    ( A ) ORGANISM: Homo sapiens (  x i  ) SEQUENCE DESCRIPTION: SEQ ID NO:191:

CAGAAGGTAA GTGATA      16

( 2 ) INFORMATION FOR SEQ ID NO:192:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:192:

TTGACTCTAG ATGCTG      16

( 2 ) INFORMATION FOR SEQ ID NO:193:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:193:

GTAGAGGTAA AGTATT      16

( 2 ) INFORMATION FOR SEQ ID NO:194:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:194:

CTCTGTTTAG CTCCTT      16

( 2 ) INFORMATION FOR SEQ ID NO:195:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:195:

TCTCAGGTGA GCAGTA        16

( 2 ) INFORMATION FOR SEQ ID NO:196:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:196:

TTGTCCTTAG TGATAT        16

DETECTION OF MUTATIONS IN THE HUMAN ATM GENE

FIELD OF THE INVENTION

This invention pertains to methods for detecting mutations in the human ATM gene, involving the use of the polymerase chain reaction to amplify and compare DNA samples obtained from normal and test patients.

BACKGROUND OF THE INVENTION

The hereditary disease ataxia-telangiectasia (AT) is characterized by a broad spectrum of clinical findings including progressive cerebellar ataxia, telangiectasia, immunodeficiency, chromosomal instability, underdevelopment of some organ systems, increased susceptibility to malignancy, and hypersensitivity to ionizing radiation (reviewed in Gatti et al., Nature 336:577–580, 1991). Cells from AT patients display a phenotype in culture such as increased sensitivity to killing by ionizing radiation and radiomimetic chemicals, radioresistant DNA synthesis, and failure of cell cycle checkpoint controls after exposure to radiation (Taylor et al., Nature 258:427–429 (1975); Young and Painter, Hum. Genet. 82:113–117 (1989); Beamish and Lavin, Int. J Radiat. Biol. 65:175–184 (1994)). As AT patients characteristically develop leukemia or lymphoma at a young age, it is important in view of their extreme radiation sensitivity that physicians administering therapeutic radiation be aware that these patients have AT. However, as AT is a rare disease, accurate diagnosis is not always accomplished, and these patients sometimes experience fatal radiation burns as a result of cancer therapy.

Although AT itself is a rare condition, those who are heterozygous for this disease (carriers) may suffer risks that have only recently come to light. Carriers are clinically asymptomatic, but epidemiologic studies of AT families have suggested that they may be at increased risk for several types of cancer, particularly female breast cancer (Swift et al., N. Eng. J Med. 316:1289 1294 (1987); Pippard et al., Cancer Res. 48:2929–2932 (1988); Borresen et al., Genes, Chrom. & Canc. 2:339 340 (1990); Swift et al., N. Eng. J Med. 325:1831 1836 (1991)). Cell lines from AT heterozygotes display levels of radiation sensitivity intermediate between those of AT patients and normal controls (Paterson et al., Cancer Res. 39:3725 3734 (1979), Weeks et al., Radiat. Res. 128:90 99 (1991). This observation, along with epidemiologic evidence of increased radiation exposure among those obligate AT heterozygotes who did develop breast cancer, prompted Swift et al. (1991) to propose that the increase in breast cancer they observed in AT heterozygotes may have occurred through a radiation mediated mechanism. Furthermore, breast cancer incidence in atomic bomb survivors and in individuals who have experienced significant medical or occupational exposures to radiation suggest that radiation exposure is a risk factor for breast cancer (Boice and Monson, J Natl. Cancer Inst. 59:823 832 (1977); Boice et al., Radiat. Res. 73:373 390 (1978); Tokunaga et al., Radiat. Res. 112:243 272 (1987).

According to estimates based on epidemiological studies of blood relatives of AT patients, about 0.5–1.4% of the U.S. population is heterozygous for the trait (Swift et al., Am. J Hum. Genet. 39:573–583 (1986); Nowak, Science 268:1700–1701 (1995)). Accordingly, as much as 8% of breast cancer could be associated with the carrier state. This would mean that a defective ATM gene is the most common single cause of hereditary breast cancer. Thus, there is substantial interest in identifying women who are carriers so that they can take steps to avoid radiation exposure. For example, a woman who knew that she carried a defective ATM gene might take extra care to avoid occupational exposure to radiation. It has even been suggested that diagnostic x-rays, such as used in mammograms, could cause breast cancer in female carriers, and that such women should utilize other forms of early breast cancer detection (Swift et al., 1987; Science 268:1700–1701 (1995)).

Some studies have even suggested that all cancer patients could benefit if AT carriers were identified and removed from the pool of patients used to determine the most effective yet safe dose of radiation for treating various cancers (Norman et al., Am. J Clin. Oncol. 11:84–88 (1988)). Norman et al. calculated that in theory, the cure rates for several types of cancer could be increased by removing the radiation-sensitive population and treating the remaining patients more aggressively. Because of their sensitivity to radiation, carriers who continued to receive the lower doses of radiation would be expected to achieve comparable levels of cure to the non-carriers who received the higher doses. However, at the present time no method exists for identifying carriers other than by assigning probabilities of the carrier state based on an individual's relationship to an AT patient.

In view of its importance in predisposing individuals to cancer, the ATM gene has been the target of intense research. In 1995, linkage studies by an international consortium mapped the gene for AT to a 500 kb minimal region at chromosome 11q23 (Lange et al., Am. J Hum. Genet. 57:112–119 (1995)). Mutations were detected in a single gene isolated from this region in patients representing all four AT complementation groups (Savitsky et al., Science 268:1749 1753 (1995a). This gene, designated ATM, (for "AT mutated") spans approximately 150 kb of genomic DNA (Uziel et al., Genomics 33:317 320 (1996)) and generates a 12 kb transcript whose sequence has been determined and which encodes a predicted protein of 3056 amino acids (Savitsky et al., Hum. Mol. Genet. 4:2025 2032 (1995b); Byrd et al., Hum. Mol. Genet. 5:145 149 (1996)). In addition to the cDNA sequence, some of the exon intron boundaries have been mapped and limited regions of adjacent sequence determined (Uziel et al., 1996; Rasio et al., Canc. Res. 55:6053 6057 (1995)). The 3' half of the cDNA sequence contains several regions of homology with known genes suggesting functional domains. At the extreme 3' end of the predicted ATM protein is a region (approximately residues 2500–3000) sharing homology with phosphatidylinositol-3 (PI-3) kinase and a family of other genes, some involved in DNA double-strand break repair, for which specific PI-3 kinase activity has not been established. Some of these genes, which are involved in cell cycle checkpoint control or the control of telomere length in yeast, also share lesser homology with a second region of the ATM gene (approximately residues 1500–2000) (Savitsky et al. (1995a)). These homologies with known proteins suggest that the protein encoded by the ATM gene may participate in detecting DNA damage or in blocking cell division until the cell machinery has completed DNA repair.

SUMMARY OF THE INVENTION

In order to develop methods for screening individuals to determine whether they are ATM carriers, oligonucleotide primers have been designed that are suitable for use with PCR to create amplified products encompassing exons and their adjacent splice junction sequences. The design process included empirically determining the melting temperature (Tm) of candidate primers so that whenever possible, primers having the same Tm could be used for PCR. Choosing primers with the same Tm provides the advantage of permitting multiplex analysis of ATM mutations in a given DNA sample, i.e., the detection in a single assay of mutations present in several different exons.

The present invention relates, in one aspect, to a method of detecting mutations in the ATM gene that involves as a first step obtaining a sample of genome DNA from an individual suspected of carrying a mutation in the ATM gene ("test sample"). For purposes of comparison, a control sample of genome DNA is obtained from an individual who does not carry a mutation in the ATM gene. Using these two samples of DNA as templates and the above-described oligonucleotides as primers, PCR reactions are carried out to obtain amplified DNA products.

In another aspect of the invention, pairs of primers are provided that flank the exons located in coding region of the ATM gene. The sequences of representative primers are presented in Table 1, and correspond to SEQ ID NO:1 through SEQ ID NO:124. By using one of these primer pairs to prime PCR, the corresponding exon and a limited amount of its flanking intron sequence can be selectively amplified. The products thus obtained using the test and control DNA as templates are then compared by any suitable method, e.g., by gel electrophoresis, or by DNA sequencing. DNA sequencing can be used to further elucidate differences first observed by gel electrophoresis, or can be used alone to locate mutations. If this comparison reveals differences in the test and control products, one may conclude that the test sample of DNA contains a mutation in the DNA region that is flanked by the primer pair that was used in the PCR amplification.

TABLE 1

Primer sequences for amplification of ATM exons.

| SEQ ID NO. | Exon | Primer Sequence (5'→3') | Product Size (bp) |
|---|---|---|---|
| 1 | 4 | CCTCTTTCTCTCTATATATGC | 160 |
| 2 | | AATAATGGGTTACTAATCACA | |
| 3 | 5 | CAATTTTTCCTTGAAATGTGTG | 230 |
| 4 | | CAACAGAAATAAATATGAAAGAG | |
| 5 | 6 | GATGGCATGAACAGCTTTTG | 280 |
| 6 | | CTCACGCGACAGTAATCTG | |
| 7 | 7 | TAGTTGCCATTCCAAGTGTC | 288 |
| 8 | | TGAAGTTTCATTTCATGAGG | |
| 9 | 8 | TTTTTCTGTATGGGATTATGGA | 327 |
| 10 | | CATGGTCTTGCAAGATC | |
| 11 | 9 | CCCCCTGTTATACCCAGTT | 318 |
| 12 | | TGAAGAAGCAAATTCAAAACAG | |
| 13 | 10 | TTTGTGGGGAGCTAGCAGTG | 306 |
| 14 | | AAAAGCCCAAATGCCCAG | |
| 15 | 11 | AACAGCGAAACTCTGGCTC | 279 |
| 16 | | ACAAGAGATTAAAATGACACT | |
| 17 | 12 | GTTTGTTAATGTGATGGAATA | 467 |
| 18 | | GTGTGTTTATCTGTAAGTCAG | |
| 19 | 13 | ATAAAGTCTTTGCCCCTCCA | 320 |
| 20 | | AAATAAGTGGAGAGAGCCTG | |
| 21 | 14 | GGCTTTTGGTCTTCTAAGTG | 192 |
| 22 | | ATCTTTGTAATTAAAGCTATAGC | |
| 23 | 15 | GTAGTCTTTGAATGATGTAGA | 377 |
| 24 | | CTATTTCTCCTTCCTAACAGT | |
| 25 | 16 | TTCTTACAAAAGATAGAGTAT | 378 |
| 26 | | TTCCAAACAAATGTAATAATT | |
| 27 | 17 | CCAAGATCAAAGTACACTGTA | 232 |
| 28 | | CCCACTGCACTCCAGCCTGGG | |
| 29 | 18 | ATATTGGCCCTAATAGTAAAC | 291 |
| 30 | | CTTATTTACAAAGATATTTCA | |
| 31 | 19 | AATTGCTGAGATTACAGATGT | 352 |
| 32 | | ACTAAACCGTCATATTCTCCG | |
| 33 | 20 | ATATAATTAATTTCACTATAA | 391 |

TABLE 1-continued

Primer sequences for amplification of ATM exons.

| SEQ ID NO. | Exon | Primer Sequence (5'→3') | Product Size (bp) |
|---|---|---|---|
| 34 | | TACATTTAGTCAGCAACATCA | |
| 35 | 21 | CCGGCCTATGTTTATATACTT | 225 |
| 36 | | TTAACAGAACACATCAGTTAT | |
| 37 | 22 | AAAGTTATAAAATAACTGATG | 287 |
| 38 | | CTTGCATTCGTATCCACAGAT | |
| 39 | 23 | TTAGCACAGAAAGACATATTG | 259 |
| 40 | | AATTACTCATTAACAAACAAA | |
| 41 | 24 | GCAGTCTTTGTTTGTTAATGA | 274 |
| 42 | | CTATGTAAGACATTCTACTGC | |
| 43 | 25 | GTTTGTTTGCTTGCTTGTTT | 203 |
| 44 | | ATTTATGGGATATTCATAGC | |
| 45 | 26 | TGGAGTTCAGTTGGGATTTTA | 304 |
| 46 | | TTCACAGTGACCTAAGGAAGC | |
| 47 | 27 | GTTGTTTCTAGGTCCTACTCT | 333 |
| 48 | | GACTTGCTAAGTATTGTTAAC | |
| 49 | 28 | TGATACTTTAATGCTGATGGT | 409 |
| 50 | | GGTTATATCTCATATCATTCA | |
| 51 | 29 | TCCTCTTAGTCTACAGGTTG | 396 |
| 52 | | GACATTGAAGGTGTCAACCA | |
| 53 | 30 | TGGAAGTTCACTGGTCTATG | 283 |
| 54 | | TACTTTTCCTCTTTAAGATGTAT | |
| 55 | 31 | TTTATTGTAGCCGAGTATCTAA | 318 |
| 56 | | AAACAGGAAGAACAGGATAGA | |
| 57 | 32 | TGCTGAACCAAAGGACTTCT | 334 |
| 58 | | CACTCAAATCCTTCTAACAATA | |
| 59 | 33 | CAGTAAGTTTTGTTGGCTTAC | 315 |
| 60 | | CTGCTAGAGCATTACAGATTT | |
| 61 | 34 | TGTCTATAAATGGCACTTAACT | 309 |
| 62 | | CCAAGAGCAAGACTTTGCC | |
| 63 | 35 | TAGAAGTTTTCTAGTCAGATAAT | 255 |
| 64 | | AATCTGTCCTATATGTGATCC | |
| 65 | 36 | CTTGAAGTACAGAAAAACAGC | 336 |
| 66 | | GTATCATTCTCCATGAATGTC | |
| 67 | 37 | TGGAGGTTAACATTCATCAAG | 287 |
| 68 | | ATTTAACAGTCATGACCCACA | |
| 69 | 38 | GGAAAGGTACAATGATTTCCA | 312 |
| 70 | | ATGTGCAGTATCACAGCACT | |
| 71 | 39 | GTATGTTGAGTTTATGGCAGA | 376 |
| 72 | | ATCCATCTTTCTCTAGAACTG | |
| 73 | 40 | ACCAGAACCTTATAGACATAGT | 247 |
| 74 | | TTCAGCCGATAGTTAACAAGT | |
| 75 | 41 | TAAGCAGTCACTACCATTGTA | 314 |
| 76 | | ATACCCTTATTGAGACAATGC | |
| 77 | 42 | GTATATGTATTCAGGAGCTTC | 238 |
| 78 | | ATGGCATCTGTACAGTGTCT | |
| 79 | 43 | CAGAACTGTATTTCAGAATCAT | 387 |
| 80 | | ACATAACTCCTTCATAAACAGA | |
| 81 | 44 | CCAAAGCTATTTTCACAATCTT | 262 |
| 82 | | TACTGAAATAACCTCAGCACT | |
| 83 | 45 | CTCTGGTTTTCTGTTGATATC | 236 |
| 84 | | CCCCATGAAGAATCAAGTC | |
| 85 | 46 | TTTATACATGTATATCTTAGGGTTCTG | 220 |
| 86 | | TTCAGAAAAGAAGCCATGACA | |
| 87 | 47 | TATTTCCCTGAAAACCTCTTC | 233 |
| 88 | | CACTATTGGTAACAGAAAAGC | |
| 89 | 48 | TCATTTCTCTTGCTTACATGAA | 314 |
| 90 | | AAAGGAAAGTCAAGAGGTAAG | |
| 91 | 49 | ATGGTAGTTGCTGCTTTCATT | 365 |
| 92 | | TTACTAATTTCAAGGCTCTAATA | |
| 93 | 50 | AGTTGGGTACAGTCATGGTA | 230 |
| 94 | | GAAAAGATGAAGACATATTCATG | |
| 95 | 51 | TTTGAGTGATTCTTTAGATGTAT | 352 |
| 96 | | AACAACTCACTCAGTTAACTG | |
| 97 | 52 | TGTGTGATTTTGTAGTTCTGTT | 340 |
| 98 | | ACATCAAGGGGCTTATGTCT | |
| 99 | 53 | ACTTACTTGCTTAGATGTGAG | 282 |
| 100 | | CCATTTCTTAGAGGGAATGG | |
| 101 | 54 | CACTGCAGTATCTAGACAGT | 322 |
| 102 | | CTAGGAAAGACTGAATATCAC | |
| 103 | 55 | AATGTTGGGTAGTTCCTTATG | 308 |
| 104 | | GCTTTTGGATTACGTTTGTGA | |
| 105 | 56 | TGACTATTCCTGCTTGACCT | 253 |
| 106 | | TTTCACCAATTTTGACCTACAT | |
| 107 | 57 | TAACCACTATCACATCGTCAT | 385 |

TABLE 1-continued

Primer sequences for amplification of ATM exons.

| SEQ ID NO. | Exon | Primer Sequence (5'→3') | Product Size (bp) |
|---|---|---|---|
| 108 |  | CTTCCTCATTTGTAAGTATTCA |  |
| 109 | 58 | CCTTTGCTATTCTCAGATGACTCTGT | 290 |
| 110 |  | GCATTATGAATATGGGCATGA |  |
| 111 | 59 | GATCATCAAATGCTCTTTAATG | 286 |
| 112 |  | TATCTGACAGCTGTCAGCTT |  |
| 113 | 60 | GTGTATATTAGTTTAATTGAACAC | 279 |
| 114 |  | AACCTGCCAAACAACAAAGTG |  |
| 115 | 61 | TAGAAAGAGATGGAATCAGTG | 317 |
| 116 |  | ATCTTGGTAGGCAAACAACAT |  |
| 117 | 62 | AAAGTTCACATTCTAACTGGAA | 272 |
| 118 |  | ATTACAGGTGCAAAGAACCAT |  |
| 119 | 63 | GATAAAGATACGTTGACAACATTGG | 199 |
| 120 |  | GTGACTTCCTGATGAGATACACAG |  |
| 121 | 64 | CTGGTTCTACTGTTTCTAAGT | 298 |
| 122 |  | GTTTCAGTGAGGTGAACAGT |  |
| 123 | 65 | TCCTGTTGTCAGTTTTTCAGA | 354 |
| 124 |  | ACTTAAAGTATGTTGGCAGGT |  |

A number of mutations occurring in the ATM gene were analyzed in a first group of AT patients by exploiting a panel of 36 cell lines developed from these patients, as well as two control cell lines. As a first step in these analyses, cDNA was extracted from each of the cell lines, and then analyzed for "single-strand conformation polymorphisms," or "SSCP" analysis. For SSCP analysis, limited sectors of the cDNA are amplified using PCR and primers complementary to various regions of the cDNA, and the resulting DNA products analyzed on non-denaturing polyacrylamide gels. The variations from normal cDNA thus observed were confirmed by analyzing genome DNA from the same cell lines, this time using primers 29–65 from Table 1 to analyze the exons and flanking intron sequences corresponding to those regions of the cDNAs that appeared to be altered. The mutations that were detected are described in Table 2. In all cases examined, cell lines from which aberrant cDNA products were obtained also had mutations present in the genome DNA. Moreover, some of the mutations detected by analyzing genome DNA could not be detected by the cDNA analysis method. In this panel of cell lines, a total of 30 mutations were identified. Twenty-five of the 30 were distinct and most patients were compound heterozygotes, i.e., each of their alleles contained a different mutation. The sequence alterations that were detected included two nucleotide substitutions, one insertion, and 27 deletions ranging from 2–298 nucleotides. In six cases, the absence of an exon in the cDNA was found to be due to an alteration in a splicing signal sequence, rather than the deletion of the exon sequence from the ATM gene. Evidence also was observed for sequence variation in the ATM gene in two cell lines derived from individuals without a family history of AT.

TABLE 2

Sequence variants identified in the 3' half of the ATM gene.

| Cell line | Exon | cDNA change | nucleotide[a] | Protein change[b] | codon[c] | Genomic DNA change | nucleotide[a] | Comments |
|---|---|---|---|---|---|---|---|---|
| AT7LA | 12 | ΔAG | 1561 | Ter | 521 | ΔAG | 1561 | homozygous |
| GM02782 | 17 | Δ19 nt | 2251 | Ter | 750 |  |  | cryptic 3' acceptor |
| LM217[d] | 17 | Δ19 nt | 2251 | Ter | 750 |  |  | cryptic 3' acceptor |
| GM11255 | 17 | Δ217 nt | 2251 | Ter | 750 |  |  | Δ exons 17, 18 |
| AT7SE | 17 | Δ217 nt | 2251 | Ter | 750 |  |  | Δ exons 17, 18 |
| GM00637[d] | 20 | Δ283 nt | 2639 | Ter | 880 |  |  | Δ exons 20, 21 |
| AT31LA | 23 | Δ207 nt | 3078 | Δ69 aa | 1026 |  |  |  |
| AT10SE | 23 | Δ73 nt | 3109 | Ter | 1037 |  |  | Δ exons 23, 24 |
| GM08436 | 33 | ΔGATA | 4638 | Ter | 1546 | ΔGATA | 4638 |  |
| GM02782 | 40 | Δ88 nt | 5675 | Ter | 1892 |  |  | Δ exon 40 |
| AT13LA | 41 | ins 130 | 5763 | Ter | 1921 |  |  | insert between exons 40, 41 |
| AT16LA | 44 | Δ103 nt | 6096 | Ter | 2032 |  |  | Δ exon 44 |
| AT30LA[e] | 46 | Δ105 nt | 6348 | Ter | 2124 | ins G | 6348 | splices out mutant exon |
| GM02782 | 48 | Δ81 nt | 6573 | Δ27 aa | 2191 |  |  | cryptic 3' acceptor |
| AT6SE | 50 | Δ114 nt | 6976 | Δ38 aa | 2326 |  |  | Δ exon 50 |
| AT5BI | 51 | Δ34 nt | 7274 | Ter | 2425 |  |  | cryptic donor |
| GM11261 | 52 | C→T | 7327 | R→Ter | 2443 | C→T | 7327 |  |
| AT13LA | 54 | Δ159 nt | 7630 | Δ53 aa | 2544 |  |  | Δ exon 54 |
| AT4SE | 54 | Δ9 nt | 7638 | Δ3 aa | 2546 | Δ9 nt | 7638 |  |
| AT31LA | 54 | Δ9 nt | 7638 | Δ3 aa | 2546 | Δ9 nt | 7638 |  |
| AT8SE | 54 | Δ9 nt | 7638 | Δ3 aa | 2546 | Δ9 nt | 7638 | confirmed in sib, AT9SE |
| GM11261[e] | 54 | Δ298 nt | 7630 | Ter | 2544 |  |  | Δ exons 54, 55 |
|  | 55 | Δ139 nt | 7789 | Ter | 2597 |  |  | Δ exon 55 |
|  | 55 |  |  | R→S | 2642 | (A→C)Agtatgttttt | 7926 | conserved position for splicing |
| AT4SE | 55 | Δ139 nt | 7789 | Ter | 2597 | ttattaa(t→g)agGA | intron | splice acceptor mutation |
| IAT2203 | 55 | Δ139 nt | 7789 | R→Ter | 2598 | C→T | 7792 | Δ exon 55 |

TABLE 2-continued

Sequence variants identified in the 3' half of the ATM gene.

| Cell line | Exon | cDNA change | cDNA nucleotide[a] | Protein change[b] | Protein codon[c] | Genomic DNA change | Genomic DNA nucleotide[a] | Comments |
|---|---|---|---|---|---|---|---|---|
| AT13SE | 57 | Δ140 nt | 8011 | Ter | 2671 | (A→G)Ggtgagcct | 8150 | Δ exon 57 |
| GM03189 | 58 | Δ117 | 8152 | Δ39 aa | 2758 | | | Δ exon 58 |
| AT3ABR[e] | 58 | A→T | 8266 | K→Ter | 2756 | A→T | 8266 | |
| GM09587[e] | 59 | Δ150 nt | 8269 | Ter | 2758 | TG(Δgtga)gtgaca | intron | splice donor mutation |
| AT1SE | 59 | Δ150 nt | 8269 | Ter | 2758 | TG(Δgtga)gtgaca | intron | splice donor mutation |
| GM11254[e] | 62 | Δ115 nt | 8672 | Ter | 2891 | AG(g→a)taagtgata | intron | splice donor mutation |

[a]The first nucleotide of the open reading frame in the ATM gene was designated as 1.
[b]changes in which specific numbers of amino acids are indicated are predicted to be in-frame alterations.
[c]indicates the codon interrupted by mutation.
[d]cell line derived from an individual without family history of AT.
[e]alteration in cDNA previously described (Savitsky et al. 1995; Gilad et al. 1995; Telatar et al. 1996).

A second group of cell lines derived from AT patients was also analyzed using the primers of Table 1, which were derived from throughout the coding exons of the ATM gene. The results of these analyses are shown in Table 3. The cell lines used for this study were derived from individual patients, and orignially were assigned names based on the patients' initials. To protect patient confidentiality, these cell lines have been assigned letters of the alphabet as identifiers in Table 3. For these analyses, samples from AT cell lines were first investigated at the cDNA level to determine a general region in which a mutation might be found. Subsequently, exons corresponding to these "candidate" regions were amplified from genomic DNA and their DNA was sequenced. Thus, this represents the largest series of AT patients studied, to date, at both cDNA and genomic DNA levels. The most notable feature of the results is that cDNA analysis is a poor predictor of the nature of the actual mutations in most cell lines because many of the mutations lead to aberrant mRNA splicing. The underlying genomic mutations leading to splicing aberrations can often be located at sites distinct from the exons that are incorrectly spliced. In some cases, changes observed in cDNA were not confirmed as resulting directly from mutations when genomic DNA was studied.

TABLE 3

Sequence variants identified in the second panel of cells.

| Cell line | Exon | cDNA change | cDNA nucleotide | Protein change | Protein codon | Genomic DNA change | Genomic DNA nucleotide | Comments |
|---|---|---|---|---|---|---|---|---|
| a | 7 | Δ165 nt | 332 | Δ55 aa | 111 | | | Δ exon 7 |
| b | 11 | | | Ter | 393 | ΔGG | 1178 | frameshift |
| c | 11 | Δ170 nt | 1066 | Ter | 356 | | | Δ exon 11 |
| d | 12 | ins | 1608 | ins | 536 | G(g→t)taagtt | intron | retain intron 12 |
| e | 12 | ΔAG | 1561 | Ter | 521 | ΔAG | 1561 | frameshift |
| f | 15 | Δ44 nt | | | | | | |
| g | 16 | Δ126 nt | 2125 | Δ42 aa | 709 | (G(g→A)gtaggag | 2250 | Δ exon 16 |
| h | 17 | Ins 9 | 2251 | ins 3 | 751 | a(t→g)tcacaatagT | intron | new splice acceptor |
| i | 18 | Δ90 nt | 2377 | Δ30 aa | 793 | A(g→a)taagtatg | intron | Δ exon 18 |
| j | 19 | ins 1 | 2493 | Ter | 831 | ins A | 2493 | frameshift |
| h | 20 | ins 4 | 2809 | Ter | 937 | ins CTAG | 2809 | frameshift |
| k | 23 | ins 1 | 3085 | Ter | 1029 | ins A | 3085 | frameshift |
| l | 24 | | | E→Ter | 1072 | G→T | 3214 | |
| m | 24 | Δ3, ins 4 | 3408 | Ter | 1081 | ΔATC, ins TGAT | 3406 | frameshift |
| n | 25 | | | Q→Ter | 1128 | C→T | 3382 | |
| f | 26 | Δ174 nt | 3403 | Δ58 aa | 1135 | (G→A)gtatatat | 3576 | Δ exon 26 |
| o | 26 | | | | | (G→A)gtatatat | 3576 | |
| p | 26 | T→G | 3485 | L→Ter | 1162 | T→G | 3485 | |
| q | 27 | G→A | 3663 | W→Ter | 1221 | G→A | 3663 | |
| r | 27 | Δ2 nt | 3626 | Ter | 1209 | ΔAA | 3626 | frameshift |
| s | 28 | Δ1 nt | 3802 | Ter | 1268 | ΔG | 3802 | frameshift |
| t | 32 | ins 11 | 4612 | Ter | 1538 | (a→g)attatatttag | 4612 | new splice acceptor |
| u | 37 | | | Ter | 1764 | ΔC | 5290 | frameshift |
| v | 40 | ins 137 | 5763 | Ter | 1921 | gtaa(a→g)gA | intron | new splice donor |
| w | 42 | Δ88 nt | | E→Ter | | G→T | | Δ exon 42 |
| l | 43 | | | | 2032 | G→A | 6095 | |
| x | 45 | Δ341 | 6007 | Ter | 2003 | G(g→a)taagaaa | intron | multiple spliced forms |
| m | 46 | Δ105 nt | 6346 | Δ35 aa | 2116 | G(g→a)tattatgaaaa | intron | Δ exon 46 |
| y | 46 | | | Ter | 2135 | ins TT | 6404 | frameshift |
| k | 54 | | | | | ttttcttac(a→c)gC | intron | |

TABLE 3-continued

Sequence variants identified in the second panel of cells.

| | | cDNA | | Protein | | Genomic DNA | | |
|---|---|---|---|---|---|---|---|---|
| Cell line | Exon | change | nucleotide | change | codon | change | nucleotide | Comments |
| z  | 54 |         |      | Ter    |      | ΔGA          | | frameshift |
| aa | 55 | Δ64 nt  | 7863 | Ter    | 2621 | C→T          | 7865 | new splice donor |
| g  | 58 | Δ117 nt | 8152 | K→Ter  | 2714 | A→T          | 8266 | Δ exon 58 |
| p  | 58 |         |      | Ter    | 2755 | ΔATAAG       | 8264 | frameshift |
| bb | 62 | Δ115 nt | 8672 | Ter    | 2891 | G(g→a)taagtgat | intron | Δ exon 62 |
| cc | 62 | ins 1   | 8766 | Ter    | 2922 | ins T        | 8766 | frameshift |

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1 illustrates the locations of truncation mutations detected in the ATM gene. Heavy lines indicate the relative length of the predicted truncated protein. Broad areas of homology of ATM with PI-3 kinase or rad3, as delineated in Savitsky et al. (1995a) are indicated. Numbers at the ends of these lines indicate the codon at which a frameshift or truncation occurs. Numbers in parentheses indicate when more than one distinct truncation mutation was observed at a given codon.

DETAILED DESCRIPTION OF THE PREFERRED EMBODIMENT

Knowledge of the spectrum of mutations occurring in the ATM gene in AT patients is an important prerequisite for developing mutation screening strategies in the general population of individuals with or without a family history of AT, as well as for furthering the understanding of how the ATM gene product functions. The large size of the ATM gene creates significant obstacles for accomplishing these goals.

In accordance with the present invention, a PCR-based method of detecting mutations in the ATM gene is provided, comprising conducting a first and a second PCR reaction to obtain amplified DNA products, using as a template for the first PCR reaction a sample of genome DNA from an individual suspected of carrying a mutation in the ATM gene, and using as template for the second PCR reaction a sample of DNA from an individual who does not carry a mutation in the ATM gene; wherein the first and second PCR reactions both are conducted using a pair of primers selected from the primer pairs listed in Table 1, above, and then determining that the ATM gene in the first sample of DNA contains a mutation if the first amplified DNA product is different from the second amplified DNA product. Differences between the first and second DNA products are indicative of a mutation in the ATM gene, and the differences can be determined by any convenient method, for example, by DNA sequencing or by gel electrophoresis.

In one of its embodiments, the invention also includes isolated DNA molecules whose nucleotide sequences encode the mutations of a wild-type ATM gene that are described in Tables 2 and 3, and whose nucleotide sequences are determined by PCR analysis using the above-described methodology.

Potential sources of DNA for analysis include cells taken directly from the individual, for example, blood cells, or cell lines that were originally derived from an AT patient or from a control individual. Other sources of cells could include any tissue or body fluid containing cellular material.

For the subject method of analysis, DNA samples are obtained from patient and control cells, and these are used as templates for PCR reactions to obtain amplified DNA products. To prime these PCR reactions, this invention provides novel primer pairs flanking the various exons present in the ATM gene's coding region. These primer pairs are suitable for amplifying individual exons of the ATM gene, and their sequences are listed in Table I, and their sequences are shown as SEQUENCE ID NOS:1–124. In all cases, the primers are set back sufficiently far from the splice junctions so that the PCR product also includes the splice junctions, thus enabling the detection of mutations that affect splicing as well as mutations that affect only the coding regions. Mutations occurring at or near the splice junctions in genomic DNA are not detectable in assays that use cDNA as a template.

To derive primers corresponding to introns in the 3' half of the ATM coding region, a clone containing the 3' portion of the gene was sequenced using an Applied Biosystems sequencer with dye terminator chemistry. The resulting sequence revealed a total of 37 exons that encoded portions of the ATM sequence. These 37 exons correspond to exons 29–65 in Table 1. Other primers corresponding to exons in the 5' half of the gene were based on sequence provided by Y. Shiloh. These letter primers correspond to exons 1–28 in Table 1. Whenever possible, primers were designed to have similar base compositions and Tm's. The Tm's of candidate primers were determined empirically, and to the extent possible, primers with similar Tm's were selected for use in screening. Despite some variability in the Tm's of selected primers, in practice it has been observed that positive results are obtained for all primers when the annealing step is conducted at 58° C. Presently preferred primers derived in accordance with the foregoing are set forth in Table 1.

PCR was conducted according to standard methods. For analyzing genomic DNA, PCR reactions contained 50 ng of human genomic DNA as a template, 0.3 $\mu$M of each primer, 20 $\mu$M of dNTPs supplemented with $^{33}$P-DATP, 1X PCR buffer (Perkin Elmer), and 2 units of Taq polymerase (Perkin Elmer). PCR was carried out using 35 cycles of 1 minute at 94° C., 1 minute at the Tm of the primers, and 1 minute at 72° C.

The next step of the subject method was to determine whether or not a mutation is present in the AT sample of DNA by comparing the amplified DNA products from test and control DNA templates. This comparison can be performed, for example, by DNA sequencing, chromatographic analysis, gel electrophoresis, or any other convenient method.

In one embodiment of the invention, the method of analysis of the amplified PCR DNA products is a technique called "single-strand conformation polymorphism" analysis (see, e.g., Mullis et al., PCR: The Polymerase Chain Reaction, 1994). Known as "SSCP analysis," this PCR-based technique involves simultaneously labeling and amplifying the target sequence from test and control samples, heat denaturing the resulting products, and analyzing them by polyacrylamide gel electrophoresis. In SSCP analysis, several types of mutation, even including single base substitutions, typically result in a shift in the test sample relative to the control sample of the mobility of the bands detected on the final autoradiogram. These shifts apparently are caused by conformational changes caused by the mutation. This method of analysis is best suited for fragments of DNA having no more than about 400 base pairs, as for longer fragments, different conformations do not resolve well on polyacrylamide gels.

To detect mutations in the ATM gene, DNA is extracted from AT and control cells, and amplified using one or more of the primer pairs listed in Table 1, as described above. The amplified DNA products thus obtained are analyzed and compared on a polyacrylamide or agarose gel, the type and percentage of the gel being chosen to accommodate the expected DNA products.

In one of the embodiments of this invention, increased efficiency is achieved by analyzing simultaneously two or more exons of the ATM gene. This is called "multiplex analysis." For multiplex analysis, primer pairs flanking two or more exons are used to prime DNA amplification of samples of genomic DNA taken from AT cells and control cells. Optimally, each of the primers selected for this purpose have the same melting temperature (Tm), so that all of the primers being used will hybridize to the template DNA during the first step of PCR, which includes a hybridization step. If the Tm's of the primers differed by more than about 2° C., they would not hybridize efficiently and specifically under a single set of annealing conditions. However, even when primers with the same Tm's are employed, some combinations of primers do not work efficiently in multiplexed reactions. The reasons for this are unknown, but the phenomenon may occur because of some interference between primers or products during the amplification step, or because the products are not effectively resolved from each other in subsequent SSCP analyses. Thus, one aspect of this invention is the identification of primers having similar Tm's and the empiric determination that these primers can be effectively pooled for multiplex analyses. Thirteen groups of primers amenable to multiplex analysis were identified. For multiplex analysis, a wide range of DNA products may be obtained, thus it may be convenient to use a gel in which the percentage of acrylamide or agarose forms a gradient, so that the full range of fragment sizes obtained can be resolved in a single gel.

One embodiment of this invention involves multiplex analysis of DNA samples to detect mutations in the ATM gene. This method involves conducting a first and a second PCR reaction, using as template for the first PCR reaction a sample of DNA from an individual suspected of carrying a mutation in the ATM gene, and using as template for the second PCR reaction a sample of DNA from an individual who does not carry a mutation in the ATM gene, and using as primers for both the first and second PCR reactions a first and a second pair of primers selected from among the several sets of primer pairs described in Table 5. If desired, more than two pairs of primers from a one of the listed sets may be used simultaneously to prime the PCR reactions. As many as all the pairs included in a given set in Table 5 may be used simultaneously in a single PCR reaction.

In the experiments illustrated below, cDNA corresponding to the mRNA extracted from a number of cell lines from two panels of AT patients were analyzed by SSCP. The results of these analyses revealed a diverse array of alterations, the majority of which would be predicted to lead to truncation of the ATM protein. The second panel of samples was analyzed also by protein truncation testing. These apparent mutations were further analyzed in many instances by using the primers of Table 1 to amplify genome DNA from the same cell lines.

Using this approach, a total of 30 mutations from among the first panel of AT patients were analyzed, of which 25 were distinct mutations in the ATM gene. Fifteen of the mutations observed in cDNA were confirmed by amplification and sequencing of the appropriate exons from genomic DNA. In all 8 of the cell lines in which putative splicing defects were investigated, underlying mutations were detected in genomic DNA, indicating that the alterations detected in cDNA reflected mutation rather than, for example, alternative splicing. Further, in several cases it was possible to resolve whether deletions of exons observed in cDNA corresponded to the same, or distinct mutations.

The high frequency of truncation mutations observed may have important implications for ATM heterozygotes where some of these mutations may function as mild dominant negatives. The diversity of mutations detected suggests that there are a large number of different mutant ATM alleles in the general population and that none occur at a high frequency. Accordingly, these results underscore the need for methods that can detect a wide variety of mutations in ATM.

In analyzing the second panel of AT patient cell lines, 36 alterations were observed, 10 of which could be detected only by screening genomic DNA. Of the 36, 33 were confirmed at the genomic level, and of these, 31 were found in only a single cell line, again underscoring the diversity among mutations in AT patients. One notable exception to the diversity seen in ATM mutations may be a 9 nucleotide deletion at codon 2546 in exon 54 that has been independently observed in eight different AT families. Determining whether all eight of these families are truly unrelated must await detailed genetic haplotyping studies. Three of the families observed in the first panel of cell lines have this mutation, and within these three families, the mutation has been observed in association with at least two distinct haplotypes.

The results observed in this sampling of AT patients suggests that population screening approaches to evaluate the issues of AT heterozygote frequency and cancer susceptibility will have to be done by screening prospectively for mutations. In this regard, the finding that two normal cell lines each harbored single mutant ATM alleles provides some encouragement that carriers will be detected by this approach. However, it should be noted that both of these samples are long-standing, frequently passaged cell lines that did not originate in this laboratory. Without the original donor DNA to check for confirmation, the possibility that these alterations may have arisen during cell culture cannot be ruled out. A true measure of the carrier frequency will, most likely, require a survey of genomic DNA derived from primary tissue sources. Furthermore, screening methods will have to be highly efficient in order to obtain a valid measure of carrier frequency.

EXAMPLES

Example 1

Creation of Primers for SSCP Analysis of ATM Mutations

While the availability of the ATM cDNA sequence will allow mutation screening when RNA is available from the individuals undergoing screening, another convenient and readily available source of nucleic acid for screening purposes is genomic DNA extracted from body tissues or fluids, as for example, a drop of blood. In order to facilitate the analysis of genome DNA, primers have been designed that flank the intron-exon boundaries of all of the protein-encoding exons present in the ATM gene, and that provide the capacity for amplification of each exon.

A. Primers to the 3' Half of the ATM Gene

The first step in obtaining primers for this half of the ATM gene was to sequence those portions of the gene corresponding to intron sequence immediately flanking each exon in this region of the gene. To provide a template for this sequencing project, a yeast artificial chromosome (YAC clone), Y67 was kindly provided by Dr. Y. Shiloh. This YAC clone contains the entire clone 7–9 ATM sequence, which corresponds to the 3' half of the ATM mRNA. By this time the sequence of the ATM cDNA sequence had been published (Savitsky et al., 1995). Based on the cDNA sequence, PCR primers were designed that were spaced at intervals of about 300–500 bp. These primers complementary to cDNA were used in various combinations to amplify genomic regions in Y67 DNA present in extracts of total yeast DNA. By using the Expand Long Template PCR System (Boehringer Mannheim) and protocols supplied by the manufacturer, discrete products ranging up to 23 kb in size could be routinely amplified. YAC clone PCR products thus obtained were then sequenced using dye terminator chemistry on an ABI 373 sequencer (Applied Biosystems). Intron-exon boundaries were identified as positions at which the nucleotide sequences derived from YAC clone PCR products diverged from that of the cDNA. The sequences at intron-exon boundaries are shown in Table 4.

TABLE 4

Exon-intron structure of the ATM gene.

| Exon | Size (bp) | 3' splice site (acceptor) | 5' splice site (donor) | intron size (kb) |
|---|---|---|---|---|
| 29 | 65 | | . . . TTCAGGgtatgtacat[a] | 1.2 |
| 30 | 127 | actctgttagGGATTT | . . . AGCCCTgtaagtatac | 0.500[b] |
| 31 | 200 | tattttctagGATTCC | . . . AGCCCTgtaaataaca | 2.9 |
| 32 | 175 | cctatattagGCCTTC | . . . AAACAGgtaattttct | 0.519[b] |
| 33 | 165 | ttatatttagGTATTG | . . . TTGGAGgtaataaaaa | 1.5 |
| 34 | 133 | tctcttttagGAAATT | . . . CTCAGGgtgctaattt | 1.8 |
| 35 | 96 | atatttctagATAATC | . . . TTCTAGgtaaactaca | 2.1 |
| 36 | 172 | ctatatgtagAGGCTG | . . . AGATTGgtgagtattt | 1.8 |
| 37 | 142 | tttttttcagTGTCAA | . . . AAAAAGgtctcttaag | 1.0 |
| 38 | 177 | ttctttctagTTTTTA | . . . TGTGAAgtaagaagat | 1.8 |
| 39 | 178 | tatattctagGTGAAA | . . . ATTCAGgtattctatt | 3.4 |
| 40 | 88 | tgtttgtcagAGTCAG | . . . AAAGAGgtaatgtaat | 2.2 |
| 41 | 156 | ttttctttagACCTTC | . . . GAAAAGgtaatggaat | 1.9 |
| 42 | 88 | agacaaacagAAGTCT | . . . TTACAGgtaaatatta | 4.0 |
| 43 | 89 | atgttttcagGATCTT | . . . TACTAGgtaaattgca | 0.100[b] |
| 44 | 103 | tttcttatagACTACG | . . . ATTCAGgtacattttt | 1.4 |
| 45 | 149 | tcctgttttagGCCTTG | . . . CGTCAGgtaagaagtg | 2.3 |
| 46 | 105 | tatctcacagCAAAGA | . . . TGCCAGgtattatgaa | 1.4 |
| 47 | 120 | ttgctactagAGTAAA | . . . CTCAAGgtatgtaatt | 4.0 |
| 48 | 235 | tggcattcagATCAGT | . . . ACTCAGgtaaatacaa | 0.513[b] |
| 49 | 168 | ttcatttcagCTCCCT | . . . GCAGCGgttttgttttt | 1.4 |
| 50 | 114 | tcttatacagAACAAT | . . . GAAAAGgtaagatttt | 1.2 |
| 51 | 218 | tttcttgaagGCAGTA | . . . AAACAGgtaactaggt | 1.0 |
| 52 | 208 | tctatgcaagATACAC | . . . ATGAAGgcaagtgtta | 1.0 |
| 53 | 114 | ttaatggtagAGAGAC | . . . AATAATgtaagtaaac | 0.321[b] |
| 54 | 159 | tttctttacagCTAATC | . . . GATGAGgtatttggat | 0.7 |
| 55 | 139 | ttattaatagGATCGA | . . . AGAGAAgtatgttttt | 1.0 |
| 56 | 83 | ttaaatacagAAGGCA | . . . ATTAAGgtaatttgca | 1.0 |
| 57 | 141 | cttttattagGTGGAC | . . . GTTAAGgtgagccttc | 0.8 |
| 58 | 117 | tctgaaggagGGCCGT | . . . TATAAGgtaactattt | 8.0 |
| 59 | 150 | gtaactccagGTGGTT | . . . ATGATGgtgagtgaca | 3.0 |

TABLE 4-continued

Exon-intron structure of the ATM gene.

| Exon | Size (bp) | 3' splice site (acceptor) | 5' splice site (donor) | intron size (kb) |
|---|---|---|---|---|
| 60 | 166 | ctatttaaagGAGGTG | . . . CTATTGgtaatcttct | 1.4 |
| 61 | 87 | ttttctccagTTGGTT | . . . ATCTAGgtaagtaaaa | 6.0 |
| 62 | 115 | tttactttagGTGTTG | . . . CAGAAGgtaagtgata | 0.930[b] |
| 63 | 64 | ttgactctagATGCTG | . . . GTAGAGgtaaagtatt | 2.2 |
| 64 | 137 | ctctgttttagCTCCTT | . . . TCTCAGgtgagcagta | 0.106[b] |
| 65 | 184 | ttgtccttagTGATAT | | |

[a]intronic sequences are shown in lower cast and exonic sequencs in capitals
[b]complete nucleotide sequence of intron determined.

Primers for the amplification of individual exons were designed based on the flanking intronic sequences. PCR amplifications of exons from human genomic DNA were performed with the Hot Tub DNA polymerase (Amersham) using 0.3 μM of each primer. Products were resolved on 2% NuSieve-1% agarose (FMC) gels to determine the extent of amplification. Nucleotide sequencing to confirm the identity of the amplified exons was carried out as described above.

PCR and nucleotide sequence analysis revealed that in the 3' half of the gene were a total of 37 exons encoding portions of the ATM sequence (see Table 4). The exons were numbered according to the exon numbering system of Uziel et al. (1995). The sizes of the coding region exons were uniformly small, ranging from 64 bp to 235 bp. The last exon was somewhat larger, containing 181 nucleotides of coding sequences, the termination codon, TGA, and 543 nucleotides of noncoding sequences followed by the site of poly(A) addition. Splice sites all conformed to the AG/GT rule, with the exception of the splice donor site at the end of exon 24, where a GC was observed instead of a GT.

The intron lengths were estimated based on the sizes of PCR products generated with primers from adjacent exons or, in the case of introns that were smaller than 600 nucleotides, determined by direct sequence analysis. In most cases, the exon lengths reported by Uziel et al. corresponded to those found here. The estimated lengths of the 36 introns and the known coding sequence sum to 72 kb.

The amplified intron sequences were scanned by Southern analysis using a $CA_{(10)}$ oligonucleotide probe for microsatellite repeats that might have utility in loss of heterozygosity studies. A long repeat sequence which proved to be polymorphic was identified in the intron between exons 34 and 35. A GenBank search revealed that it corresponded to the previously identified marker D11S2179 (Vanagaite et al., Hum. Genet. 95:451–454 (1995)).

PCR primers were designed to amplify each of these 37 exons for mutation screening. The design process was not straightforward, as a number of specific constraints on primer design had to be addressed in order to obtain primers useful for mutation screening: (1) The overall size of the resulting PCR product needed to be kept within the size range that would give optimal mutation detection by SSCP, typically 150–400 base pairs. (2) The primers need to be placed far enough away from sequences at or near splice junctions so that changes at these positions are both assayed by SSCP and detectable when the primers are used for nucleotide sequencing. (3) The primers must not match any repetitive sequences which might tend to lead to mispriming. (4) Primer sequences were chosen such that there would be only minimal differences in melting temperatures across the panel of primers. This latter feature has two advantages. First, it allows multiplexing of reactions, i.e. the pooling of several different primer sets into a single reaction vessel for simultaneous PCR and gel analysis. Second, it allows the analysis of multiple exons in a single PCR run. For example, all 65 coding exons of the ATM gene could be screened in a single 96 well microtiter dish in a single PCR run if the appropriate primers could be designed.

Primer pairs designed for the 3' half of the gene are shown as exon numbers 29 through 65 in Table 1. PCR product sizes were selected to be in the range of 200–400 bp. An important feature of the primers in Table 1 is that in order to facilitate the detection of mutations in the conserved sequences near the splice junctions, the locations of the primers were set back approximately 40 nucleotides from the splice junctions. Some exceptions were made in cases where there was a high AT content, or repeated sequences which might result in PCR artifacts.

To the extent possible, primers were designed to have a standard melting temperature of 58° C. to allow for possible multiplex analysis. The Tm for each primer had to be determined empirically, as no reliable means exists for accurately predicting the Tm of an oligonucleotide probe.

Multiplex analysis is an important aspect of an ATM screening assay, as the capacity to screen for several mutations in one assay greatly enhances the commercial feasibility of widespread screening to detect carriers. However, it was found that simply matching annealing temperatures was a poor guide as to which primers would yield reproducible products upon pooling. Accordingly, the determination of which ATM primer sets can be multiplexed was accomplished by empirical experimentation. It was found, for example, that in many combinations, one set of primers appeared to suppress amplification by others by an unknown mechanism. Thirteen combinations of exon primers found to be amenable to multiplex amplification are illustrated in Table 5.

TABLE 5

ATM multiplex primer sets.

| Multiplex Set | Exons | Product Sizes (bp) |
|---|---|---|
| 1 | 60, 63, 64 | 279, 199, 298 |
| 2 | 32, 49, 37 | 334, 365, 287 |
| 3 | 35, 36, 42 | 255, 336, 238 |
| 4 | 29, 65, 38, 44 | 396, 354, 312, 262 |
| 5 | 5, 7, 8, 14 | 230, 288, 327, 192 |
| 6 | 4, 24, 9 | 160, 274, 318 |
| 7 | 17, 19, 28 | 232, 352, 409 |
| 8 | 13, 15, 29 | 320, 377, 116 |
| 9 | 33, 56 | 315, 253 |
| 10 | 30, 47 | 283, 233 |
| 11 | 30, 47, 51, 61 | 283, 233, 352, 317 |
| 12 | 30, 39, 47, 54, 61 | 283, 376, 233, 308, 317 |
| 13 | 38, 50, 52, 62 | 312, 230, 340, 272 |

Since the PCR amplifications used initially to determine intron-exon boundaries are carried out with YAC DNA as a template, it was necessary to confirm the sequences using human genomic DNA from an unaffected individual. Such tests were conducted and results indicated that the YAC and human genomic sequences were concordant at all positions. Only one discrepancy was observed, A for G at position 5222 changing an Asp codon to Asn. In this case, the difference was with the published sequence of the cDNA.

B. Primers for the 5' Half of the ATM Gene

With the subsequent publication of the nucleotide sequence of the 5' half of the ATM coding region (Savitsky et al. 1995b; Byrd et al. 1996), primers were designed empirically for amplifying exons in this half of the gene as well (Table 1, corresponding to exons 4 28).

Example 2

Methods

A. Cell Lines

A first panel of 38 cell lines (including two controls), and a second panel of 28 cell lines, all derived from unrelated individuals, were assayed for variation in the ATM gene. Cell lines designated AT#SE (Seattle) have not been previously described. Those designated AT#LA (Los Angeles) were from the UCLA Ataxia-Telangiectasia Research Laboratory. Cell lines designated with GM numbers were obtained from the NIGMS Mutant Cell Repository. In some cases, isolates of the same cell line, obtained separately from the UCLA laboratory and from NIGMS, were studied and were found concordant in all cases. All of the above were Epstein Barr virus transformed lymphoblastoid cell lines. The SV40 transformed normal fibroblast cell lines LM217 and GM00637, and the AT fibroblast cell line, AT5BI, were provided by Dr. Leon Kapp (Stanford Research Institute).

B. SSCP Analyses

These analyses were performed as a first estimation of whether the cell lines contained aberrent ATM genes. RNA was prepared from the cell lines using Trizol reagent (Gibco-BRL) and protocols from the manufacturer. Randomly primed first strand cDNA was prepared using reverse transcriptase. The nucleotide sequence of the ATM cDNA was kindly provided by Dr. Y. Shiloh, prior to publication (Savitsky et al. 1995a,b). Sets of PCR primers complementary to the cDNA and spaced 250–500 nucleotides apart were used to amplify overlapping fragments of the cell line-derived ATM cDNA sequence. Amplifications were done in two stages with the second amplification using hemi- or fully nested primers to ensure high specificity. Prior to SSCP analysis, all PCR products were examined by electrophoresis in 1.5% LE agarose gels. Larger deletions and insertions were usually apparent at this stage due to substantial shifts in the migration of the bands as compared with bands from normal cDNA. PCR products were then assayed for sequence variation by SSCP essentially as described by Orita et al. (*Genomics* 5:874–879 (1989)), a procedure that relies on denaturing the DNA samples prior to electrophoresis on non-denaturing gels. With this procedure, even small deletions and changes in nucleotide sequence usually result in mobility shifts. All samples were analyzed on 0.5 X MDE® gels, both with and without glycerol (5–10%) present in the gel.

C. Nucleotide Sequencing

Variant bands and, in some cases, normal bands identified in SSCP gels were individually excised from the gels. DNA was eluted from gel slices by soaking overnight in 10 mM Tris pH (7.0), reamplified, and sequenced using fluorescent dye terminators on an ABI 373A sequencer. All nucleotide sequences were determined on both strands.

D. Genomic DNA Assays

Confirmations of alterations detected in cDNA were carried out using genomic DNA as a template. Primers used were those described in Table 1, which were designed such that they would amplify the exon of interest as well as 40 nucleotides of flanking intronic sequence on each side of the exon. Intron nucleotide sequences flanking exons of interest were determined as described in Example 1 by sequencing long PCR products generated from a YAC clone containing the entire ATM gene. Variation in amplified exons was assessed by SSCP and nucleotide sequencing, as was done for product derived from cDNA templates, or, in some cases, by cloning of the amplification product and nucleotide sequencing of a minimum of 6 independent clones.

Example 3

A. Sequence Variation in the ATM Gene

For the first stage in this analysis, PCR primers corresponding to ATM mRNA were synthesized based on the published ATM cDNA sequence. These primers were designed to amplify overlapping cDNA fragments of between 250 and 500 nucleotides, spaced over the length of the cDNA. To use these primers for the detection of mutations, ATM cDNA was synthesized from mRNA extracted from each of two panels of cell lines derived from AT patients. The first of these was a panel of 38 cell lines, including two control cell lines and 36 lymphoblastoid cell lines derived (as described in Example 2) from unrelated AT patients. The second of these was a panel of 28 lymphoblastoid cell lines derived from unrelated AT patients provided by investigators at UCLA. The cell lines serving as controls for the first panel were two SV40-transformed fibroblast cell lines derived from donors without a family history of AT.

i. Analysis of First Panel of Cells

For analysis of the first panel of cell lines, PCR amplification products from all 38 cell lines were screened for sequence variation by SSCP under 2 different gel conditions, namely, with and without 5–10% glycerol present in the gels. All bands exhibiting aberrant migration on SSCP gels were excised, re-amplified, and sequenced on both strands.

Using this approach, 30 instances of sequence variation in the 3' half of the ATM gene were detected (Table 2). The sequence alterations observed included two nucleotide substitutions, one insertion and 27 deletions ranging from 2 to 298 nucleotides. The recent publication of the exon-intron structure of the ATM gene (Uziel et al., 1996) allowed many of these deletions to be identified as corresponding to the failure to correctly splice one or two exons. The bias in favor of detection of large deletions may reflect the relatively large sizes of these PCR products. These deletions were usually of sufficient size that they were apparent by visual examination of PCR products in agarose gels prior to SSCP analysis.

Twenty-five different variants were represented among the 30 sequence differences observed in the 3' half of the gene, i.e., exons 29–62, and no one variant was detected more than three times. In the cases of two pairs of cell lines where the same alteration in cDNA was detected (AT4SE/IAT2203 and AT7SE/GM11255), the genotyping of two markers flanking ATM (namely, D11S1818 and D11S1819) and one marker within the gene (D11S2179) revealed that the cell lines shared no alleles at any of these markers. This indicates that the losses of exons detected in these cell lines resulted from independent and distinct mutations. In the case of the AT4SE and IAT2203 cell lines, subsequent analysis of genomic DNA provided additional evidence that they harbored distinct mutations, both leading to the incorrect splicing of exon 55.

In virtually all cases where an abnormal SSCP pattern was observed, bands corresponding to the normal allele were present as well. Thus, most AT patients appeared to be compound heterozygotes, i.e., these patients had different mutations in each of their two ATM alleles. The one exception was a patient, AT7LA, from the pedigree originally used to localize the ATM gene (Gatti et al. (1988)). This patient was homozygous for a two nucleotide deletion in codon 521. Interestingly, this same mutation has also been described in one patient from the UK (Byrd et al. (1996)).

In the absence of functional data, it is difficult to conclusively determine whether an observed variation in sequence represents a true deleterious mutation. However, 19 of the 25 unique variants observed in the 3' half of the gene would be predicted to truncate the ATM protein, in most cases by frameshifting, and thus are likely to represent deleterious changes to the protein. Moreover, the presence of these mutations in cell lines derived from AT patients provides circumstantial evidence for their deleterious character.

FIG. 1 indicates the locations of these truncation mutations, which are broadly distributed throughout the ATM protein. Although there is no obvious clustering of these mutations that might point to critical domains of the ATM protein, it may be significant that the two regions of homology to other genes (the rad 3 domain and PI 3 kinase domain) both lie in the 3' half of ATM and would thus be affected by the majority of these truncation mutations.

Among variants observed in more than one patient, the most frequent was a nine nucleotide deletion occurring at codon 2546 in exon 54. This mutation was observed in three unrelated AT families and was confirmed in one family in a second sibling (AT8SE and AT9SE). In all these cases, it was also confirmed by amplification from genomic DNA. Genotyping of these families with microsatellite markers flanking and within the ATM gene (D11S1818, D11S1819, and D11S2179) suggested that the mutation was present on at least two distinct haplotypes. Among alterations reported in the ATM gene in AT families to date, this is the most frequently observed change (8/103 total mutations reported, 8%). (Savitsky et al. (1995a); Byrd et al. (1996); Gilad et al., Hum. Molec. Genet. 5:433 439 (1995); Telatar et al., Am. J Hum. Genet., 59:40 44 (1996)).

The deletion at codon 2546 would be predicted to delete only three amino acids and leave the reading frame intact. It has been argued that it is, indeed, a mutation, since one of the amino acids lost is conserved in a S. cerevisiae homologue of ATM, TEL1 (Morrow et al. (1995)). However, its modest predicted effect on the protein might also be consistent with a polymorphic allele of ATM. The deletion results in the loss of a unique XbaI restriction site, thus making it possible to assay for this mutation by amplification of genomic DNA and subsequent XbaI digestion of the product. When this assay was performed on the parents of the CEPH gene mapping families (n=75) no examples of the deletion were detected, indicating that this alteration is not a common allele of ATM.

In addition, closely spaced mutations occurring on different alleles can sometimes give the appearance of homozygosity. For example, in the case of AT4SE, one allele bearing a 139 nucleotide deletion corresponding to the loss of exon 55 failed to amplify, while the other allele, with a 9 nucleotide deletion in exon 54 did. Thus the resulting SSCP pattern contained only bands corresponding to the 9 nucleotide deletion and no normal allele, suggesting homozygosity for the 9 nucleotide deletion. Subsequent examination of products amplified with other primer sets, as well as identification of a mutation in the exon 55 splice acceptor by analysis of genomic DNA helped to clarify the mutations occurring in this sample.

Several of the AT cell lines screened here have been previously studied (Savitsky et al. (1995a); Gilad et al. (1995); Telatar et al. (1996)). The current study extends these observations by providing the identity of the second mutant allele in compound heterozygous patients. For example, SSCP screening of AT3LA revealed the previously reported splicing defect leading to the loss of exon 55 or both exons 54 and 55 (Savitsky et al. 1995a). However, a band corresponding to the normal allele was also present. Further screening of the gene revealed two additional alterations, a conservative substitution (ACA→ATA) at position 2438, and a nonsense substitution (AAG→TAG) at 2443. The nonsense substitution at codon 2443, which would truncate the protein, is a clearly deleterious mutation. In order to determine the relationship between these observed alterations, fragments spanning all of the changes were amplified from cDNA, separated on an SSCP gel and sequenced. In this analysis, fragments with 1 or 2 exons deleted always had the normal sequence at codons 2438 and 2443 indicating that the null mutation and the splicing aberration correspond to different alleles.

Putative splicing mutations were examined in AT30LA, GM11261, AT4SE, IAT2203, AT1SE, GM09587, GM11254 and AT13SE. In the case of AT30LA, an insertion of a single G residue in exon 46 was detected which would lead to frameshifting and premature termination. A fraction of the cDNA had this exon deleted, presumably allowing the production of a shortened, in-frame transcript, which could still have some partial function. A similar observation was made for IAT2203, where a single nucleotide substitution creating a stop codon was detected in exon 55. This exon was deleted in cDNA from IAT2203.

GM11261 was only one of three cell lines in which deletion of exon 55 was detected in cDNA. Genomic analysis of the other two cell lines, AT4SE and IAT2203, revealed that each of the three cell lines had a distinct mutation that affected splicing of this exon. A similar analysis of GM09587 and AT1SE, which each delete exon 59 in cDNA, revealed that they shared a common mutation at the 3' splice donor site of exon 59.

Other observed splicing variants resulted from mutations in conserved residues in and around the splice donor and acceptor sequences (Table 2). Perhaps the most interesting was detected in GM11261 which, in both this study and that of Savitsky et al. (1995a), displayed a complex splicing pattern in which either exon 55 alone, or both exons 54 and 55 were deleted. Genomic nucleotide sequence analysis of exons 54 and 55 and their flanking and intervening introns revealed that the penultimate nucleotide of exon 55 was altered (A→C). In eukaryotic exons, this residue is most often A (60%) and least often C (12%) (Hawkins, 1991). Further, exon 55 of ATM already has another non-standard residue, A, at the adjacent last position of the exon, which in most eukaryotic exons is G (79%) (Hawkins (1991)). Thus this combination of mutated and non-standard residues at the splice junction likely reduces the match to optimal splicing sequences to such a level that frequent aberrant splicing events are observed.

ii. Analysis of Second Panel of Cells

A second set of 28 AT lymphoblastoid cell lines also was examined for mutations. All members of this panel were analyzed both at the cDNA level and at the genomic DNA level, using the methods described above. The results are shown in Table 3. A total of 36 alterations were noted (see Table 3), of which 33 could be confirmed by genomic screening. Indeed, 10 mutations were detected only by screening genomic DNA and were not detected by cDNA screening methods. Nine of the 33 mutations detected by genomic screening affected splice sites, and thus were only detectable by genomic screening. Overall, most mutations were distinct. Only 2 mutations, a nucleotide substitution leading to a stop codon in exon 58, and a splice site mutation affecting exon 62 were found in common between cell lines listed in Tables 2 and 3 (MCR and AT3BR, AJO and GM11254). A third mutation affecting the splicing of exon 26 was observed in 2 cell lines in Table 3. Thus the results of the analysis of cell lines in Table 3 confirms that the number of distinct ATM mutations in the population must be quite large, and highlights the power of genomic DNA analysis to reliably identify these mutations.

B. Confirmation of Variation in Genomic DNA

All prior published studies of ATM gene variation have relied on cDNA templates because of the relatively large size of the gene to be surveyed and because of the unavailability of alternative methods. Many of the changes detected, both in this study and in previous ones (Savitsky et al. (1995a); Byrd et al. (1996); Gilad et al. (1995); Telatar et al. (1996)) appear to correspond to splicing errors. In order to confirm results obtained with cDNA as the SSCP template in this first panel of cells, intronic nucleotide sequences were determined, using primers 12, 33, 46, 52, 54, 55, 56, 57, 58, 59, and 62 of Table 1, so that selected samples could be analyzed after amplification from genomic DNA. PCR reactions contained 50 ng of human genomic DNA as a template, 0.3 $\mu$M of each primer, 20 $\mu$M of dNTPs supplemented with 33P-dATP, 1X PCR buffer (Perkin Elmer) and 2 units of Taq polymerase (Perkin Elmer). PCR was carried out using 35 cycles of 1 minute at 94° C., 1 minute at the Tm of the primers, and 1 minute at 72° C.

As indicated in Table 2, many of the alterations in cDNA were further elucidated by genomic DNA analysis. For example, the short nucleotide deletions in cDNA from AT7LA, GM08436, AT4SE, AT31LA and AT8SE and the nucleotide substitutions in exon 52 of GM11261 and exon 58 of AT3ABR were all confirmed by analysis of genomic DNA. As discussed above, the splicing variant detected in GM11261 was also confirmed by genome DNA analysis.

C. AT Heterozygotes

Two fibroblast cell lines not derived from AT patients or their families, GM00637 and LM217, were screened by SSCP for mutations across the entire ATM cDNA sequence. Both GM00637 and LM217 have been used frequently as normal controls in radiation biology experiments, and their responses to radiation are well characterized (e.g. Lehmann et al., *Int. J. Radiat. Biol.* 49:639–643 (1986); Ziv et al., *Som. Cell. Molec. Genet.* 21:99–111 (1995)). Despite their apparently normal radiation phenotypes, aberrant splicing products were detected in both LM217 and GM00637 that would be predicted to truncate the ATM protein. The normal radiation phenotype of these cell lines probably means that the observed mutations occurred during culture, and that only a fraction of the cells in the line bear the mutation. In the case of GM00637, the observed alteration corresponding to the loss of two exons and was not detected in any other cell line screened. In LM217, an aberrantly migrating SSCP band containing a deletion of the first 19 nucleotides of exon 17 was detected. This alteration was also observed in an AT cell line GM02782 (Table 2). The last 5 nucleotides of the deleted region, TGCAG, conforms to the consensus sequence for a 3' splice acceptor, YNCAG, suggesting that it may be serving as a cryptic splice acceptor sequence. Nucleotide sequencing of the normal and variant SSCP bands derived from LM217 cDNA revealed that the final nucleotide of exon 16 was, in both cases, a G rather than the C reported for the normal ATM sequence (Savitsky et al. 1995b; Uziel et al. 1996). While this change may be responsible for the observed alteration in splicing, its observation in both normal and mutant SSCP products, along with the 250-fold greater preference for G as opposed to C at the −1 position of 5' splice donors (Hawkins, 1991) may be more consistent with an error in the original ATM sequence.

D. Detection of Mutations in Genome DNA

Although SSCP analysis of cDNA from AT patients can provide useful indications of mutations in the ATM gene, direct analysis of genome DNA offers several advantages. When cDNA is analyzed, the results occasionally can be misleading. For example, in the studies described above, analyses of cDNA derived from AT30LA, GM11261, IAT2203, AT13SE, GM09587, AT1SE, and GM11254 cells yielded amplified products whose analyses indicated that exons 46, 54, 55, 57, 59, 59, and 62, respectively, were missing. However, subsequent analysis of genome DNA using primers flanking these same exons (Table 1, primer pairs Nos. 46, 54, 55, 57, 59, 59, and 62), revealed that the exons were not deleted from the ATM gene in those cells, but rather that an error in the splicing signal adjacent to these exons resulted in the exons being eliminated from the mRNA. These experiments illustrate that more accurate information concerning the nature of deletions can be obtained from analyzing genome DNA rather than cDNA.

Another advantage is that for clinical testing, genome DNA samples are generally easier to obtain than mRNA samples. Typically, obtaining sufficient amounts of mRNA requires culturing the cells obtained from each patient, a procedure that is costly and time-consuming. Also, mRNA is far more susceptible to degradation than DNA, hence DNA is more convenient to extract and store.

Example 4

Detection Methods for Mutations in ATM Gene

The mutations described in Example 3 are potentially detectable at either the protein or nucleic acid level. At the protein level, they can be detected by the use of specific antibodies that recognize each truncated or altered protein but that do not recognize the normal ATM protein. Methods are known for the production of monoclonal antibodies to specific protein sequences and their use to detect their targets such as in radioimmunoassays or by microscopy on tissue sections. The antibodies could be labeled with either a radioactive moiety or a chromophore.

At the nucleic acid level, additional methods for detection of these mutations include, for example, hybridization assays using allele specific oligonucleotides designed so that they form stable hybrids with only the mutated form of the gene. Standard techniques useful for designing such oligonucleotides are found in the art, as, for example, in Sambrook et al., Molecular Cloning, 2d ed., 1989, which is hereby incorporated by reference. Other methods for detecting the mutations could include ligation chain reaction assays in which the ability of two oligonucleotides to be ligated together is allele specific, or, as described above, methods in which restriction enzyme cutting of a PCR product is used to assay for allele specific sequence differences in instances where the mutation alters a restriction site. An example of the latter is the deletion at codon 2546 which, as described in Example 3, results in the loss of an XbaI site. Additional guidance for mutation detection methods are found in the art, as for example, in Cotton, R. G., *Mutation Research* 285:125–144 (1993), which is hereby incorporated by reference.

In other aspects of the screening assay, multiplex screening is utilized, which involves analyzing genome DNA with the simultaneous use of several primer pairs having the same melting temperature, each pair flanking a different exon, as, for example, using the primer sets in Table 5. SSCP analysis of the resulting products in a single assay permits the detection of a mutation in any of the several targeted introns or in their splice junction regions.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of detecting mutations in the ATM gene comprising the steps of:
  (a) conducting a first and a second PCR reaction to obtain a first and a second amplified DNA product, using as template for the first PCR reaction a first sample of DNA from an individual suspected of carrying a mutation in the ATM gene, and using as template for the second PCR reaction a second sample of DNA from an individual who does not carry a mutation in the ATM gene, and using as primers for the first and second PCR reactions a pair of primers selected from the group consisting of SEQ ID NOS:1 and 2; SEQ ID NOS:3 and 4; SEQ ID NOS:5 and 6; SEQ ID NOS:7 and 8; SEQ ID NOS:9 and 10; SEQ ID NOS:11 and 12; SEQ ID NOS:13 and 14; SEQ ID NOS:15 and 16; SEQ ID NOS:17 and 18; SEQ ID NOS:19 and 20; SEQ ID NOS:21 and 22; SEQ ID NOS:23 and 24; SEQ ID NOS:25 and 26; SEQ ID NOS:27 and 28; SEQ ID NOS:29 and 30; SEQ ID NOS:31 and 32; SEQ ID NOS:33 and 34; SEQ ID NOS:35 and 36; SEQ ID NOS:37 and 38; SEQ ID NOS:39 and 40; SEQ ID NOS:41 and 42; SEQ ID NOS:43 and 44; SEQ ID NOS:45 and 46; SEQ ID NOS:47 and 48; SEQ ID NOS:49 and 50; SEQ ID NOS:51 and 52; SEQ ID NOS:53 and 54; SEQ ID NOS:55 and 56; SEQ ID NOS:57 and 58; SEQ ID NOS:59 and 60; SEQ ID NOS:61 and 62; SEQ ID NOS:63 and 64; SEQ ID NOS:65 and 66; SEQ ID NOS:67 and 68; SEQ ID NOS:69 and 70; SEQ ID NOS:71 and 72; SEQ ID NOS:73 and 74; SEQ ID NOS:75 and 76; SEQ ID NOS:77 and 78; SEQ ID NOS:79 and 80; SEQ ID NOS:81 and 82, SEQ ID NOS:83 and 84; SEQ ID NOS:85 and 86; SEQ ID NOS:87 and 88; SEQ ID NOS:89 and 90; SEQ ID NOS:91 and 92; SEQ ID NOS:93 and 94; SEQ ID NOS:95 and 96; SEQ ID NOS:97 and 98; SEQ ID NOS:99 and 100; SEQ ID NOS:101 and 102; SEQ ID NOS:103 and 104; SEQ ID NOS:105 and 106; SEQ ID NOS:107 and 108; SEQ ID NOS:109 and 110; SEQ ID NOS:111 and 112; SEQ ID NOS:113 and 114; SEQ ID NOS:115 and 116; SEQ ID NOS:117 and 118; SEQ ID NOS:119 and 120; SEQ ID NOS:121 and 122; and SEQ ID NOS:123 and 124; and
  (b) determining that the ATM gene in the first sample of DNA contains a mutation if the first amplified DNA product is different from the second amplified DNA product.

2. The method of claim 1, wherein the difference between the first and the second amplified DNA product is determined using DNA sequencing.

3. The method of claim 1, wherein the difference between the first and the second amplified DNA product is determined using gel electrophoresis.

4. A method of detecting mutations in the ATM gene comprising the steps of:
  (a) conducting a first and a second PCR reaction to obtain a first and a second amplified DNA product, using as template for the first PCR reaction a first sample of DNA from an individual suspected of carrying a mutation in the ATM gene, and using as template for the second PCR reaction a second sample of DNA from an individual who does not carry a mutation in the ATM gene, and using as primers for the first and second PCR reactions a first and a second pair of primers selected from the group consisting of the primer pairs in one of the following sets:

Set 1: SEQ ID NOS:113 and 114, SEQ ID NOS:119 and 120, SEQ ID NOS:121 and 122;
Set 2: SEQ ID NOS:57 and 58, SEQ ID NOS:91 and 92, SEQ ID NOS:67 and 68;
Set 3: SEQ ID NOS:63 and 64, SEQ ID NOS:65 and 66, SEQ ID NOS:77 and 78;
Set 4: SEQ ID NOS:51 and 52, SEQ ID NOS:123 and 124, SEQ ID NOS:69 and 70, SEQ ID NOS:81 and 82;
Set 5: SEQ ID NOS:3 and 4, SEQ ID NOS:7 and 8, SEQ ID NOS:9 and 10, SEQ ID NOS:21 and 22;
Set 6: SEQ ID NOS:1 and 2, SEQ ID NOS:41 and 42, SEQ ID NOS:11 and 12;
Set 7: SEQ ID NOS:27 and 28, SEQ ID NOS:31 and 32, SEQ ID NOS:49 and 50;
Set 8: SEQ ID NOS:19 and 20, SEQ ID NOS:23 and 24, SEQ ID NOS:51 and 52;
Set 9: SEQ ID NOS:59 and 60, SEQ ID NOS:105 and 106;
Set 10: SEQ ID NOS:53 and 54, SEQ ID NOS:87 and 88;
Set 11: SEQ ID NOS:53 and 54, SEQ ID NOS:87 and 88, SEQ ID NOS:95 and 96, SEQ ID NOS:115 and 116;
Set 12: SEQ ID NOS:53 and 54, SEQ ID NOS:71 and 72, SEQ ID NOS:87 and 88, SEQ ID NOS:101 and 102, SEQ ID NOS:115 and 116; and
Set 13: SEQ ID NOS:69 and 70, SEQ ID NOS:93 and 94, SEQ ID NOS:97 and 98, SEQ ID NOS:117 and 118; and (b) determining that the ATM gene in the first DNA sample contains a mutation if the first amplified DNA product is different from the second amplified DNA product.

5. A purified DNA molecule consisting of a polynucleotide sequence selected from the group consisting of SEQ ID NOS:51, SEQ ID NOS:52, SEQ ID NOS:53, SEQ ID NOS:54, SEQ ID NOS:55, SEQ ID NOS:56, SEQ ID NOS:57, SEQ ID NOS:58, SEQ ID NOS:59, SEQ ID NOS:60, SEQ ID NOS:61, SEQ ID NOS:62, SEQ ID NOS:63, SEQ ID NOS:64, SEQ ID NOS:65, SEQ ID NOS:66, SEQ ID NOS:67, SEQ ID NOS:68, SEQ ID NOS:69, SEQ ID NOS:70, SEQ ID NOS:71, SEQ ID NOS:72, SEQ ID NOS:73, SEQ ID NOS:74, SEQ ID NOS:75, SEQ ID NOS:76, SEQ ID NOS:77, SEQ ID NOS:78, SEQ ID NOS:79, SEQ ID NOS:80, SEQ ID NOS:81, SEQ ID NOS:82, SEQ ID NOS:83, SEQ ID NOS:84, SEQ ID NOS:85, SEQ ID NOS:86, SEQ ID NOS:87, SEQ ID NOS:88, SEQ ID NOS:89, SEQ ID NOS:90, SEQ ID NOS:91, SEQ ID NOS:92, SEQ ID NOS:93, SEQ ID NOS:94, SEQ ID NOS:95, SEQ ID NOS:96, SEQ ID NOS:97, SEQ ID NOS:98, SEQ ID NOS:99, SEQ ID NOS:100, SEQ ID NOS:201, SEQ ID NOS:102, SEQ ID NOS:103, SEQ ID NOS:104, SEQ ID NOS:105, SEQ ID NOS:106, SEQ ID NOS:107, SEQ ID NOS:108, SEQ ID NOS:109, SEQ ID NOS:110 , SEQ ID NOS:103, SEQ ID NOS:112, SEQ ID NOS:113, SEQ ID NOS:114, SEQ ID NOS:115, SEQ ID NOS:116, SEQ ID NOS:117, SEQ ID NOS:118, SEQ ID NOS:119, SEQ ID NOS:120, SEQ ID NOS:121, SEQ ID NOS:122, SEQ ID NOS:123, and SEQ ID NOS:124.

6. An isolated DNA molecule consisting of a nucleotide sequence encoding a mutation of a wild-type ATM gene wherein the DNA molecule has at its 5' terminus at least one nucleotide sequence selected from the group consisting of SEQ ID NOS:1 through 124.

* * * * *

UNITED STATES PATENT AND TRADEMARK OFFICE
CERTIFICATE OF CORRECTION

PATENT NO. : 5,770,372
DATED : June 23, 1998
INVENTOR(S) : P. Concannon

Page 1 of 2

It is certified that error appears in the above-identified patent and that said Letters Patent is hereby corrected as shown below:

| COLUMN | LINE | |
|---|---|---|
| [56] Pg. 1, col. 1 | Refs. Cited (Other Publs., Item 1) | "Savinsky" should read --Savitsky-- |
| [56] Pg. 1, col. 1 | Refs. Cited (Other Publs., Item 1) | "1993" should read --1995-- |
| [56] Pg. 1, col. 2 | Refs. Cited (Other Publs., Item 9) | "pigmentation" should read --pigmentosum-- |
| [56] Pg. 1, col. 2 | Refs. Cited (Other Publs., Item 13) | "of cancer of" should read --of cancer in-- |
| 1 | 32 | "bums" should read --burns-- |
| 15 | 54 | "are carried" should read --were carried-- |
| 18 | 36 | "XbaI" should read --XbaI-- |
| 132 (Claim 5, | 24 line 19) | "NOS:201," should read --NO:101,-- |

UNITED STATES PATENT AND TRADEMARK OFFICE
CERTIFICATE OF CORRECTION

PATENT NO. : 5,770,372
DATED : June 23, 1998
INVENTOR(S) : P. Concannon

It is certified that error appears in the above-identified patent and that said Letters Patent is hereby corrected as shown below:

| COLUMN | LINE | |
|---|---|---|
| 132 (Claim 5, | 28 line 23) | "NOS:103," should read --NO:111,-- |
| 132 (Claim 6, | 34 line 2) | After "ATM gene" insert --,-- |

Signed and Sealed this

Twenty-seventh Day of June, 2000

Attest:

Q. TODD DICKINSON

*Attesting Officer*     *Director of Patents and Trademarks*